(12) United States Patent
Seo et al.

(10) Patent No.: US 10,031,483 B2
(45) Date of Patent: Jul. 24, 2018

(54) WEARABLE DEVICE

(71) Applicant: Samsung Electronics Co., Ltd., Suwon-si, Gyeonggi-do (KR)

(72) Inventors: Ho-Seong Seo, Suwon-si (KR); Dong-Churl Kim, Ansan-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/010,554

(22) Filed: Jan. 29, 2016

(65) Prior Publication Data

US 2016/0223992 A1 Aug. 4, 2016

(30) Foreign Application Priority Data

Jan. 29, 2015 (KR) .................. 10-2015-0014559

(51) Int. Cl.
| | |
|---|---|
| *G04B 37/14* | (2006.01) |
| *F16M 13/04* | (2006.01) |
| *A44C 5/14* | (2006.01) |
| *G04G 19/00* | (2006.01) |
| *G04G 19/10* | (2006.01) |
| *G06F 1/16* | (2006.01) |
| *G04G 17/02* | (2006.01) |
| *A61B 5/00* | (2006.01) |

(52) U.S. Cl.
CPC .......... *G04B 37/1486* (2013.01); *A44C 5/147* (2013.01); *F16M 13/04* (2013.01); *G04G 17/02* (2013.01); *G04G 19/00* (2013.01); *G04G 19/10* (2013.01); *G06F 1/163* (2013.01); *A61B 5/681* (2013.01)

(58) Field of Classification Search
CPC .......... G06F 1/163; G06F 1/189; H02J 7/025
See application file for complete search history.

(56) References Cited

U.S. PATENT DOCUMENTS

| | | | | |
|---|---|---|---|---|
| 5,742,256 A | * | 4/1998 | Wakabayashi | ......... H01Q 1/273 224/178 |
| 5,886,669 A | * | 3/1999 | Kita | ...................... H01Q 1/273 343/700 MS |
| 6,158,884 A | * | 12/2000 | Lebby | .................... G04B 47/00 224/165 |
| 6,200,018 B1 | | 3/2001 | Dubugnon et al. | |

(Continued)

FOREIGN PATENT DOCUMENTS

| | | |
|---|---|---|
| CN | 103 885 332 A | 6/2014 |
| CN | 104188284 A | 12/2014 |

(Continued)

*Primary Examiner* — James Wu
*Assistant Examiner* — Michael Matey
(74) *Attorney, Agent, or Firm* — Jefferson IP Law, LLP

(57) ABSTRACT

A wearable device is provided. The wearable device includes a first strap portion attached or detached from a body portion and provided to allow the body portion to be worn on a human body, a second strap portion provided in the body portion to be exchanged with the first strap portion, electrically connected to the body portion, and having at least one member to provide a signal generated from the members to the body portion, and a connecting portion electrically connecting the body portion with the first strap portion or electrically connecting the body portion with the second strap portion.

36 Claims, 34 Drawing Sheets

(56) References Cited

U.S. PATENT DOCUMENTS

| | | | | |
|---|---|---|---|---|
| 6,238,083 B1* | 5/2001 | Hirano | A44C 5/14 224/168 |
| 6,619,835 B2* | 9/2003 | Kita | A44C 5/0015 368/10 |
| 8,459,825 B2* | 6/2013 | Trzecieski | H01M 2/1022 362/103 |
| 8,467,270 B2* | 6/2013 | Gossweiler | G04G 17/06 345/173 |
| 8,482,909 B2 | 7/2013 | Douglas | |
| 8,613,544 B2* | 12/2013 | Kitahara | B29C 70/70 368/282 |
| 8,624,554 B2* | 1/2014 | Ajagbe | H04M 19/08 320/114 |
| 8,787,006 B2* | 7/2014 | Golko | G06F 1/163 361/679.03 |
| 8,967,437 B2 | 3/2015 | Wilson | |
| 9,523,965 B2* | 12/2016 | Liao | G04G 17/06 |
| 9,553,625 B2* | 1/2017 | Hatanaka | H04B 1/385 |
| 9,766,655 B2* | 9/2017 | Farjami | G06F 1/163 |
| 2001/0043514 A1* | 11/2001 | Kita | A44C 5/0015 368/281 |
| 2005/0012671 A1* | 1/2005 | Bisig | G04G 21/04 343/718 |
| 2005/0048804 A1* | 3/2005 | Henriet | H01Q 1/273 439/37 |
| 2007/0064542 A1* | 3/2007 | Fukushima | G04B 37/1486 368/282 |
| 2008/0259552 A1 | 10/2008 | Calvarese | |
| 2010/0112949 A1* | 5/2010 | Kim | H01R 13/2421 455/41.3 |
| 2011/0003665 A1 | 1/2011 | Burton et al. | |
| 2011/0053666 A1* | 3/2011 | Kang | H04M 1/02 455/575.6 |
| 2011/0221688 A1* | 9/2011 | Byun | H04B 1/385 345/173 |
| 2012/0194976 A1* | 8/2012 | Golko | G06F 1/163 361/679.01 |
| 2014/0083133 A1 | 3/2014 | Lee et al. | |
| 2014/0098649 A1* | 4/2014 | Tschumi | G04B 37/1486 368/282 |
| 2014/0362544 A1* | 12/2014 | Han | G04G 17/06 361/749 |
| 2014/0378853 A1 | 12/2014 | McKinney et al. | |
| 2015/0241911 A1* | 8/2015 | Lim | G06F 1/163 361/679.03 |
| 2015/0338880 A1* | 11/2015 | Sato | G06F 1/163 361/679.03 |
| 2016/0062392 A1* | 3/2016 | Townsend | G06F 1/163 361/679.03 |
| 2016/0322745 A1* | 11/2016 | Shedletsky | H01R 13/6278 |
| 2016/0363957 A1* | 12/2016 | Stroetmann | G06F 1/163 |

FOREIGN PATENT DOCUMENTS

| | | |
|---|---|---|
| DE | 20 2010 013 569 U1 | 2/2011 |
| EP | 1 835 704 A2 | 9/2007 |
| EP | 2 813 907 A2 | 12/2014 |
| KR | 10-1335344 B1 | 11/2013 |
| WO | 2012-094503 A2 | 7/2012 |

\* cited by examiner

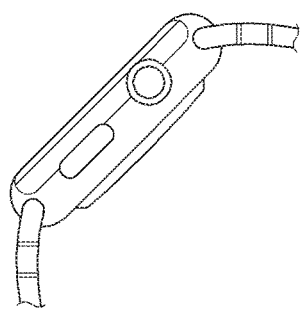 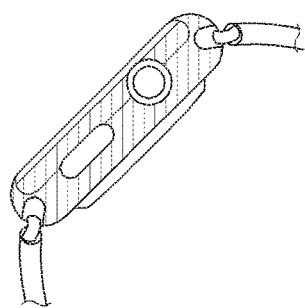 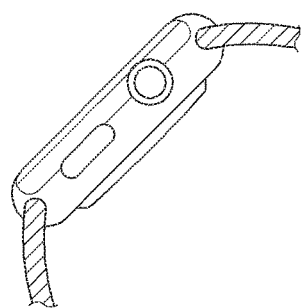
FIG.10A   FIG.10B   FIG.10C
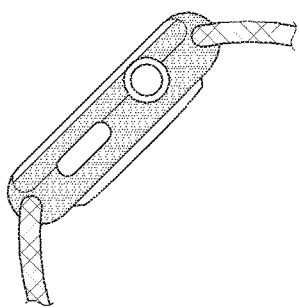 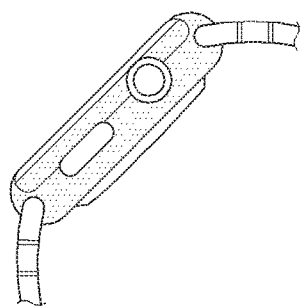 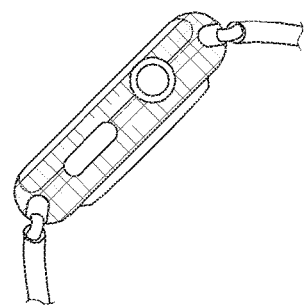
FIG.10D   FIG.10E   FIG.10F

WEARABLE DEVICE

CROSS-REFERENCE TO RELATED APPLICATION(S)

This application claims the benefit under 35 U.S.C. § 119(a) of a Korean patent application filed on Jan. 29, 2015 in the Korean Intellectual Property Office and assigned Serial number 10-2015-0014559, the entire disclosure of which is hereby incorporated by reference.

TECHNICAL FIELD

The present disclosure relates to wearable devices, e.g., wearable devices that are provided to be put on a user's body.

BACKGROUND

Generally, wearable electronic devices, such as watches, smartwatches, bio signal measuring devices, may be put on a user's body, e.g., the user's wrist. A wearable device may include a watch body or a wearable electronic device body and connecting bands (also referred to as straps) for allowing the watch body or the wearable electronic device body to be worn on the user's body.

A pair of connecting bands may be provided at opposite positions of the body. Respective first ends of the connecting bands may be coupled to the body, and respective second ends of the connecting bands may be coupled with each other.

Wearable devices need to be formed to be more lightweight and portable as compared with other portable electronic devices to be worn on the user's body.

Accordingly, the size of the body is limited, rendering it difficult to equip various modules therein.

Different modules may be mounted in the wearable device depending on the user's needs.

Therefore, a need exists for a wearable device in which a functional connecting band having various modules, as well as a normal connecting band may be coupled with a body portion in an exchangeable and compatible manner.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a wearable device in which a functional connecting band having various modules, as well as a normal connecting band may be coupled with a body portion in an exchangeable and compatible manner.

According to an embodiment of the present disclosure, there is provided a wearable device in which, when a functional connecting band having various modules is coupled with a body portion of the wearable device, diverse connecting structures may be provided between the body portion and the functional connecting band.

According to an embodiment of the present disclosure, there is provided a wearable device in which a normal connecting band and a functional connecting band may be easily attached and detached from a body portion.

According to an embodiment of the present disclosure, there is provided a wearable device in which, when a normal connecting band is coupled with a body portion, or a functional connecting band having various modules is coupled with the body portion in a way of being compatible with the normal connecting band, the body portion may detect whether the coupled band is the normal connecting band or the functional connecting band and may detect a signal from the functional connecting band to execute various user settings depending on the detected signal.

In accordance with an aspect of the present disclosure, a wearable device is provided. The wearable device includes a body portion of the wearable device, a first strap portion attached or detached from the body portion and provided to allow the body portion to be worn on a human body, a second strap portion provided in the body portion to be exchanged with the first strap portion, electrically connected to the body portion, and having at least one member to provide a signal generated from the members to the body portion, and a connecting portion electrically connecting the body portion with the first strap portion or electrically connecting the body portion with the second strap portion.

According to embodiments of the present disclosure, the normal strap portion (referred to as the "first strap portion") may be coupled to the body portion of the wearable device. Further, the functional strap portion (referred to as the "second strap portion") may be coupled with the body portion in an exchangeable and compatible manner, which is equipped with various selective functions, such as recharging the body portion, and the functions of a speaker, a camera, a flash, a location-based service, a haptic mode, and a healthcare mode.

Further, according to embodiments of the present disclosure, the second strap portion with the member according to the user's needs may be coupled with the body portion, allowing the wearable device to be customized to have the user's desired function according to the user's taste or selection.

Further, according to embodiments of the present disclosure, when the second strap portion having various functions is coupled to the body portion, there may be various electrical connection structures between the body portion and the second strap portion, including an adapter, a spring pin connecting member or a pogo pin connecting member.

Further, according to embodiments of the present disclosure, the first and second strap portions may be easily attached or detached from the body portion of the wearable device depending on the structure of the connecting portion of the first and second strap portions.

Further, according to embodiments of the present disclosure, when the first strap portion is coupled to the body portion of the wearable device or the second strap portion having the member with various functions is coupled to the body portion in a way of being compatible with the first strap portion, the body portion may detect whether the first strap portion or the second strap portion is coupled, and the body portion may detect a signal from the second strap portion to execute various user settings depending on the detected signal.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 10A to 10F and 11A to 11F are views illustrating diverse shapes, structures, and materials of a first strap portion or a second strap portion in a wearable device according to an embodiment of the present disclosure;

Throughout the drawings, like reference numerals will be understood to refer to like parts, components, and structures.

DETAILED DESCRIPTION

Figure 1:
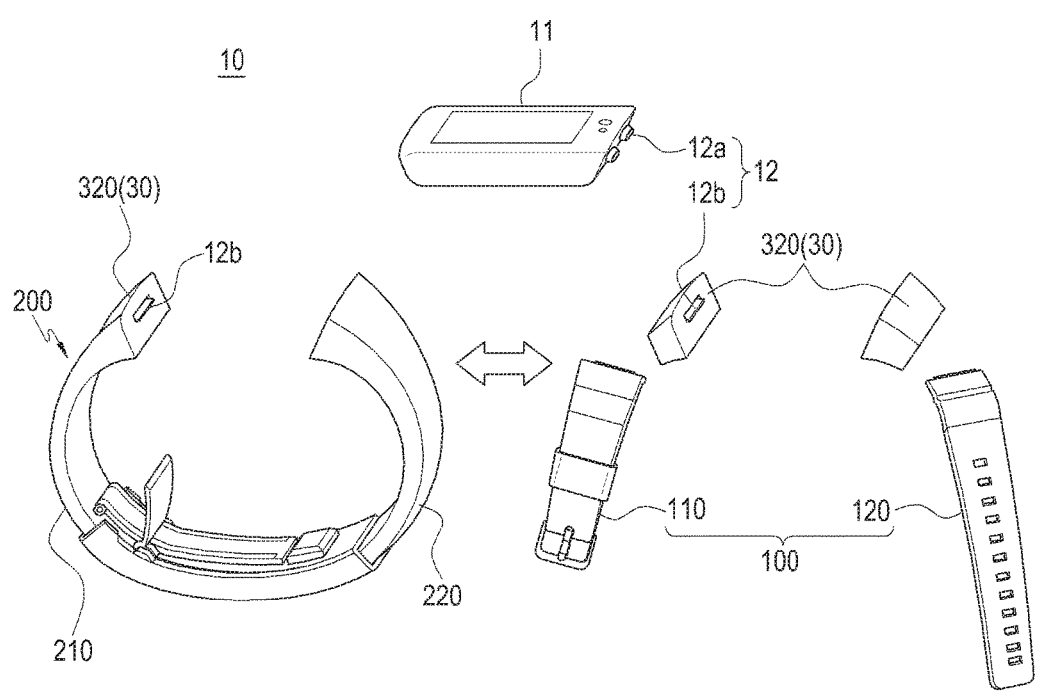
FIG. 1 is a view schematically illustrating a wearable device according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The terms coming with ordinal numbers, such as 'first' and 'second,' may be used to denote various components, but the components are not limited by the terms. The terms are used only to distinguish one component from another. For example, a first component may be denoted a second component, and vice versa without departing from the scope of the present disclosure. The term "and/or" may denote a combination(s) of a plurality of related items as listed or any of the items.

The terms "front surface," "rear surface," "upper surface," and "lower surface" are relative ones that may be varied depending on directions in which the figures are viewed, and may be replaced with ordinal numbers, such as "first" and "second." The order denoted by the ordinal numbers, first and second, may be varied as necessary.

The terms as used herein are provided merely to describe some embodiments thereof, but not to limit the present disclosure. It is to be understood that the singular forms "a," "an," and "the" include plural references unless the context clearly dictates otherwise. It will be further understood that the terms "comprise" and/or "have," when used in this specification, specify the presence of stated features, integers, operations, elements, and/or components, but do not preclude the presence or addition of at least one other feature, integer, operation, element, component, and/or group thereof.

Unless otherwise defined, all terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal detect unless expressly so defined herein.

As used herein, the term "wearable device" may denote any electronic device that may be worn on the user's wrist, including, but not limited to, a typical type of analog or digital wristwatch, a smartwatch, and a bio signal measuring device.

The wearable device may communicate with an external electronic device, e.g., a server or may perform tasks by interworking with such an external electronic device. For example, the wearable device may transmit images captured by its camera and/or location information detected by its sensor to the server via a network and may store and display data transmitted from an electronic device interworking therewith. The network may include, but is not limited to, a mobile or cellular communication network, a local area network (LAN), a wireless local area network (WLAN), a wide area network (WAN), the internet, a small area network (SAN), and the like.

For example, the electronic device interworking with the wearable electronic device may be a smartphone, a mobile phone, a navigation device, a game device, a television (TV), a head unit for vehicles, a laptop computer, a tablet computer, a personal media player (PMP), a personal digital assistant (PDA), and the like. The electronic device may be implemented as a pocket-sized portable communication terminal with a radio communication function. According to an embodiment of the present disclosure, the electronic device may be a flexible device or a flexible display.

Figure 2:
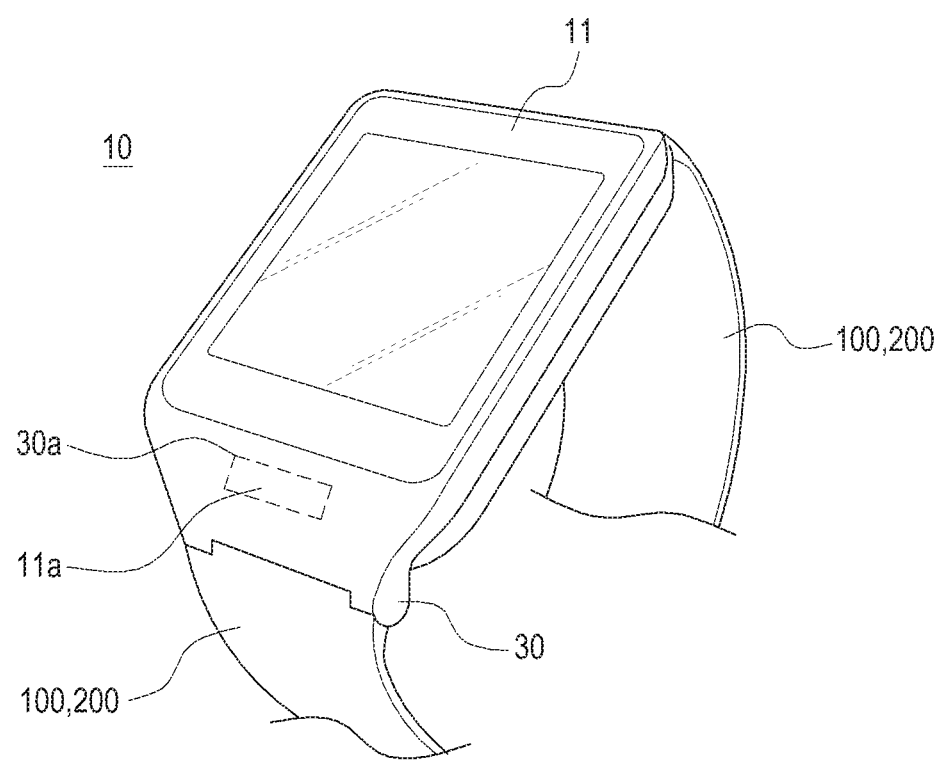
FIG. 2 is a view schematically illustrating a wearable device according to an embodiment of the present disclosure.
Figure 3:
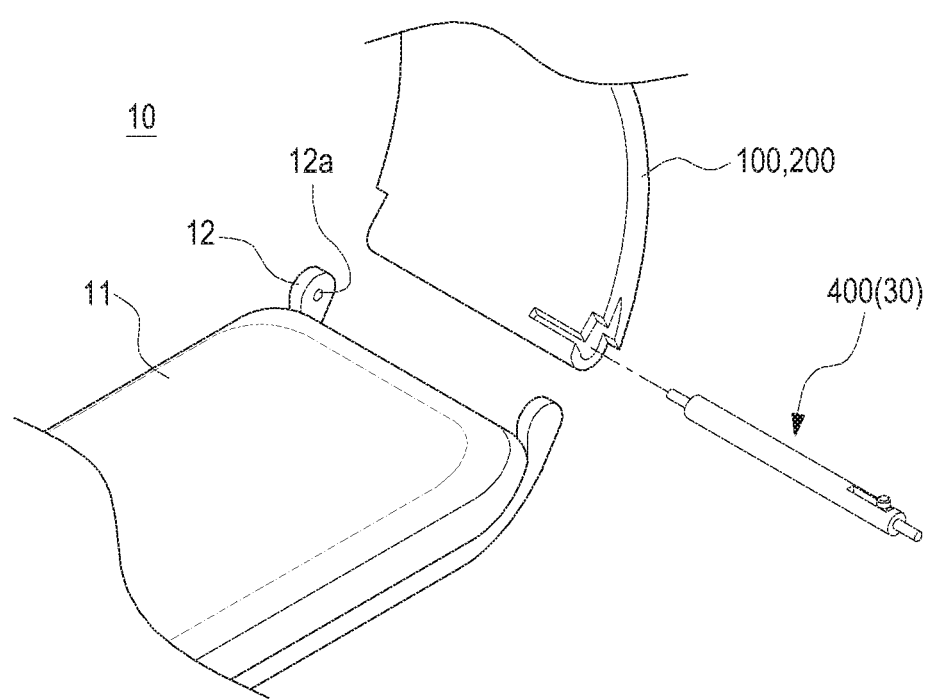
FIGS. 3 to 9 are views illustrating methods for coupling a body portion with a first strap portion or a second strap portion in a wearable device according to an embodiment of the present disclosure.
Figure 4:
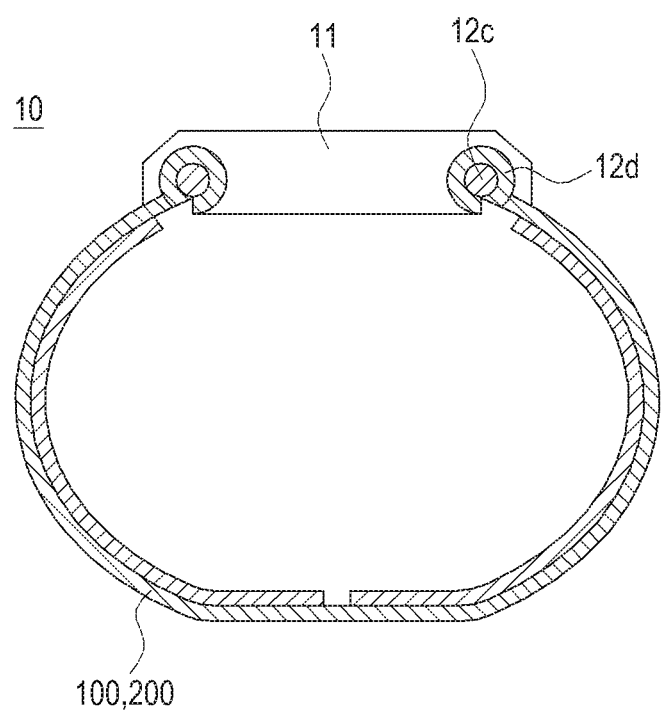
Figure 5:
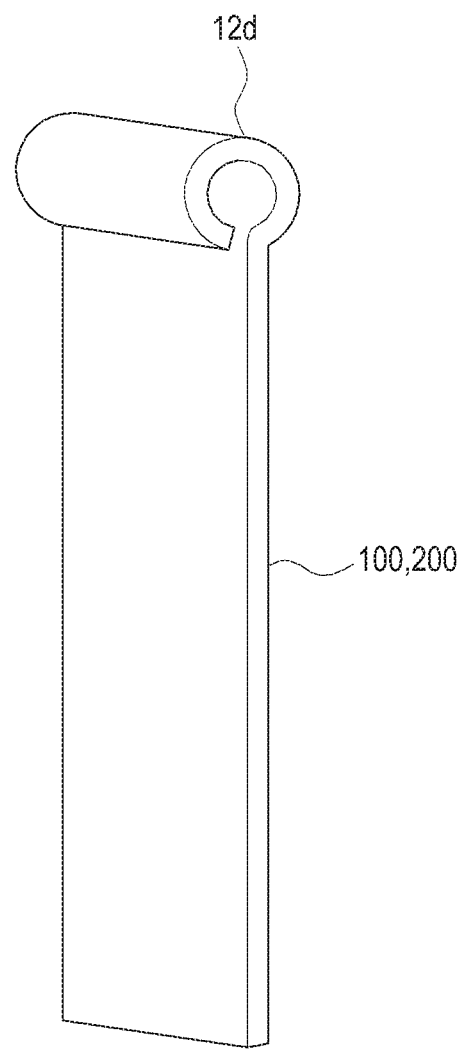

FIG. 1 is a view schematically illustrating a wearable device according to an embodiment of the present disclosure. FIG. 2 is a view schematically illustrating a wearable device according to an embodiment of the present disclosure.

Referring to FIGS. 1 and 2, a wearable device 10 according to an embodiment of the present disclosure may include a body portion 11, a first strap portion 100, a second strap portion 200, and a connecting portion 30.

The body portion 11 may be a watch module of the analog or digital watch or a display device of the wearable electronic device or a module equipped with various multimedia functions, and may be a module for detecting a bio signal. Further, the display device of the wearable electronic device may be integrated with a touch panel to be used as an input device, and the bio signal detecting module may include, e.g., electrode pads for measuring the user's heartbeat. Hereinafter described is a wearable electronic device put on the user's wrist as an example of the wearable device.

FIGS. 3 to 9 are views illustrating methods for coupling a body portion with a first strap portion or a second strap portion in a wearable device according to an embodiment of the present disclosure.

Referring to FIGS. 3 to 9 (together with FIGS. 1 and 2), a coupling portion 12 may be provided between the body portion 11 and each of the first strap portion 100 and the second strap portion 200 to detachably couple the first and second strap portions 100 and 200 to the body portion 11. According to an embodiment of the present disclosure, various changes in shape may be made to the coupling portion 12 depending on the shape of the connecting portion 30 or the type of connecting to the first strap portion 100 or the second strap portion 200. According to an embodiment of the present disclosure, there is described an example in which the coupling portion 12 is coupled to the connecting portion 30, such as an adapter portion 300 placed in the first strap portion 100 or the second strap portion 200 (refer to FIG. 1 and FIG. 14 to be described below). The adapter portion 300 may be connected to opposite ends of the first strap portion 100 or the second strap portion 200. The adapter portion 300 may include a coupling portion (hereinafter, "second coupling portion 12b") that may be coupled or decoupled from a coupling portion (hereinafter, "first coupling portion 12b") provided at both ends of the body portion 11. When the body portion 11 is seated on an upper portion of the adapter portion 300 or a midway portion of the adapter portion 300, the first coupling portion 12a of the body portion 11 may be coupled with the second coupling portion 12b of the adapter portion 300. As the body portion 11 is fitted from an upper side of the adapter portion 300 or a midway portion of the adapter portion 300 and is seated, the body portion 11 may be coupled to the first strap portion 100 or the second strap portion 200. Although not shown, a releasing button may be provided at a side of the body portion 11 or the adapter portion 300 to release the coupling between the first coupling portion 12a and the second coupling portion 12b when pressed.

Unlike the structure in which the body portion 11 and the first and second strap portions 100 and 200 are coupled with the adapter portion 300, a pin-type coupling portion 12, such as a spring pin-type connecting member, may be used for the coupling. In such case, the coupling portion 12 may be provided to be projected from both ends of the body portion 11 facing each other. As both ends of the spring pin-type connecting member are fitted and coupled into the coupling portion 12 shaped as coupling holes 12a, the coupling portion 12 may be coupled with the first strap portion 100 or the second strap portion 200 (refer to FIGS. 3 and 24). Accordingly, the ends of the coupling portion 12 inserted between ends of the first strap portion 100 or ends of the second strap portion 200 and projecting from both side surfaces may be coupled with a pair of first strap portions 100 separately formed from each other or a pair of second strap portions 200 separately formed from each other between the coupling holes 12a of the body portion 11 by a connecting member 400, such as a connecting pin or fixing pin. Further, when the first strap portion 100 or the second strap portion 200 is compatibly coupled to the body portion 11 through the pin-shaped coupling portion 12, the coupling portion 12 connecting the second strap portion 200 with the body portion 11 may be provided as the connecting portion 30 to be electrically connected with each of the second strap portion 200 and the body portion 11. Unlike this, the coupling portion 12 coupling the first strap portion 100 compatible with the second strap portion 200 to the body portion 11 may be provided to be limited from electrically contacting the body portion 11. In other words, a short circuit that may occur when the connecting member 400 electrically contacts the body portion 11 may be prevented, resultantly preventing malfunctions or damage to the body portion 11 due to the short circuit.

According to an embodiment of the present disclosure, the coupling portion 12 may be provided so that the body portion 11 may be coupled with the first and second strap portions 100 and 200 through their mutual coupling structure without separate members, such as the pin-shaped coupling portion. For example, the body portion 11 may have, at both ends thereof, opening-shaped hooking guides 12c to which an end of the first strap portion 100 or the second strap portion 200 may be fitted. Further, the end of the first strap portion 100 or the second strap portion 200 may have a hooking protrusion 12d that may be seated in the hooking guide 12c and may be fastened as the end of the first strap portion 100 or the second strap portion 200 is slid (refer to FIGS. 4 and 5). For example, as the hooking protrusion 12d formed in the end of the first strap portion 100 or the second strap portion 200 is engaged and coupled with the hooking guide 12c of the body portion 11, a coupling may be made only with the coupling structure formed in the first strap portion 100 or the second strap portion 200. Although a coupling by the sliding structure has been described in connection with the present embodiment of the present disclosure, the coupling structure between the body portion 11 and the first and second strap portion 100 and 200 is not limited thereto. For example, there may be provided a coupling structure, such as a hook coupling or a press-fitting structure, and other various coupling structure may be used.

Figure 6:
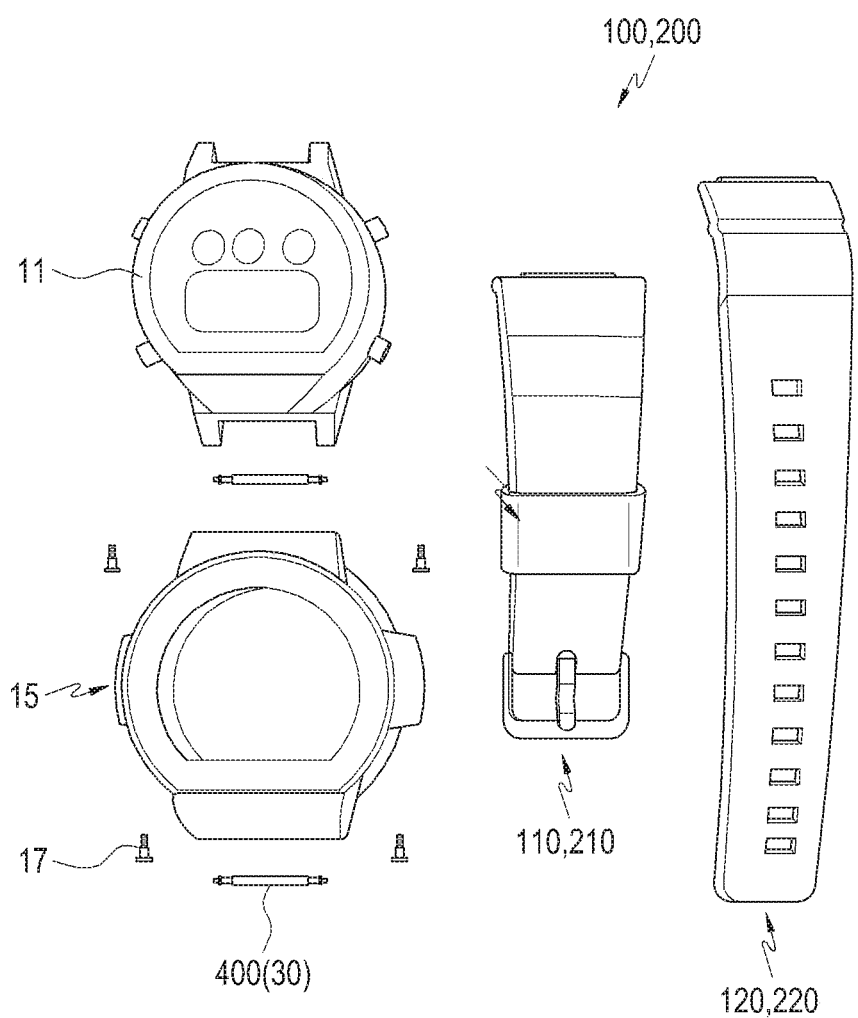
Figure 7:
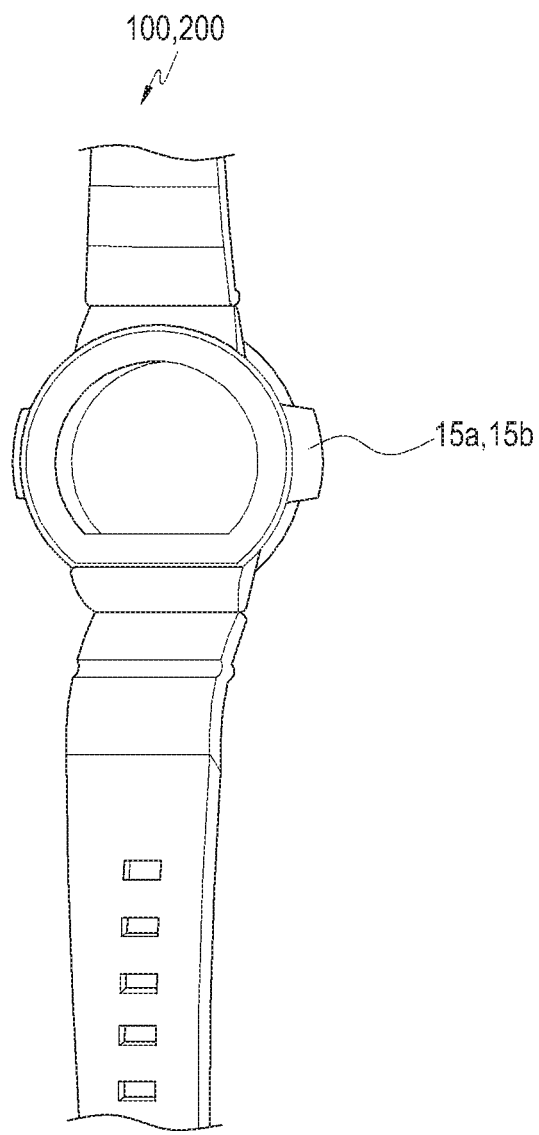

Further, the body portion 11 may have a body portion bezel (hereinafter, a "bezel portion 15") provided to cover the body portion 11 around the body portion 11 and having the first strap portion 100 and the second strap portion 200 coupled thereto in a compatible manner (refer to FIG. 6). As described above, when the body portion 11 is coupled with the first strap portion 100 or the second strap portion 200 through the bezel portion 15, the first strap portion 100, the second strap portion 200, and the bezel portion 15 may be coupled with each other by a connecting member 17, such as a screw, and may thus be detachably provided. Further, as described above, the bezel portion 15 where the body portion 11 is seated may be coupled with the first strap portion 100 or the second strap portion 200 only by way of the connecting member 17, such as a screw, or in addition, through a pin-shaped coupling portion 12, such as a connecting pin or fixing pin. Further, the bezel portion 15 connected with the second strap portion 200 through the pin-shaped coupling portion 12, such as a connecting pin or fixing pin, may electrically connect the body portion 11 with the second strap portion 200. For example, as the body portion 11 is inserted into the bezel portion 15, a body terminal portion 11a (refer to FIGS. 2 and 12) of the body portion 11 may be electrically connected with the connecting member of the bezel portion 15. When the second strap portion 200 is coupled with the bezel portion 15, the second strap portion 200 may be electrically connected to the connecting member by the connecting portion 30 that is described below. Further, the bezel portion (hereinafter, a "first bezel portion 15a") where the body portion 11 is seated and the first strap portion 100 may be formed as one piece, and the second strap portion 200 having functionality and a bezel portion (hereinafter, a "second bezel portion 15b") may be formed as one piece. Here, the term "one piece" may refer to two or more members being formed not to be separated from each other while coupled with each other or two members being formed in a single body as if they are formed at the same time. When the body portion 11 is fitted into the first bezel portion 15a, the body portion 11 is seated and coupled with the first bezel portion 15a to be connected with the first strap portion 100, so that the body portion 11 may be put on the user's body (refer to FIG. 7). Further, when the body portion 11 is fitted into the second bezel portion 15b, the body portion 11 is seated and coupled with the second bezel portion 15b, so that the body portion 11 is electrically connected with the second strap portion 200, and may thus be put on the user's body, allowing various functions (e.g., a speaker or camera, light emission, or battery recharge for the body portion 11) to be shared with the body portion 11.

Figure 8:
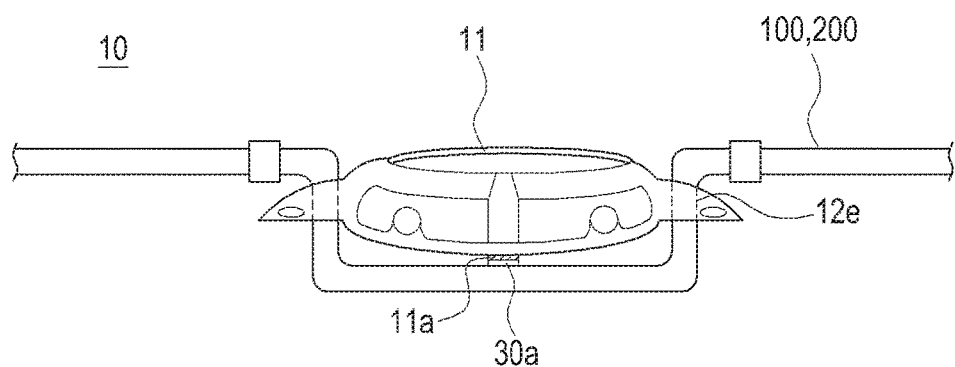
Figure 9:
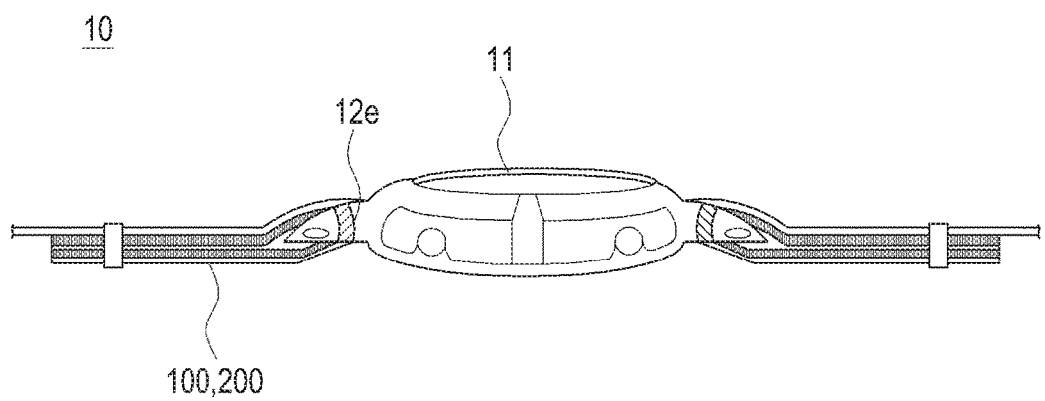
Figure 11A:
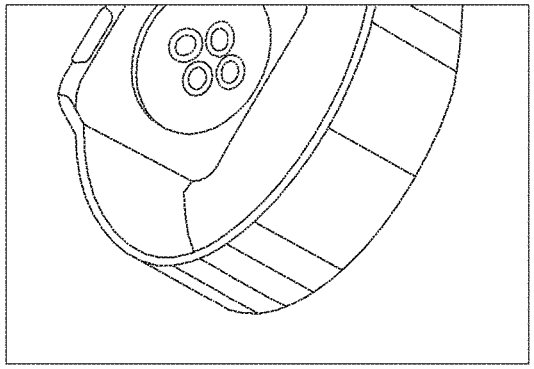
Figure 11B:
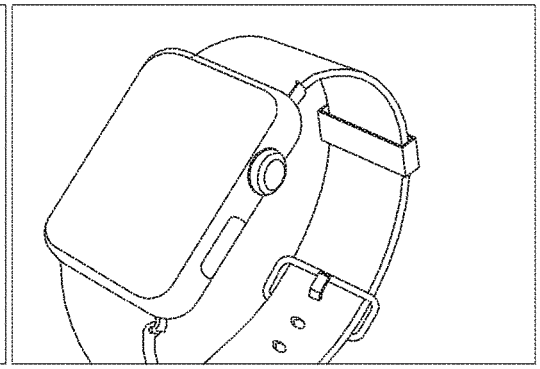
Figure 11C:
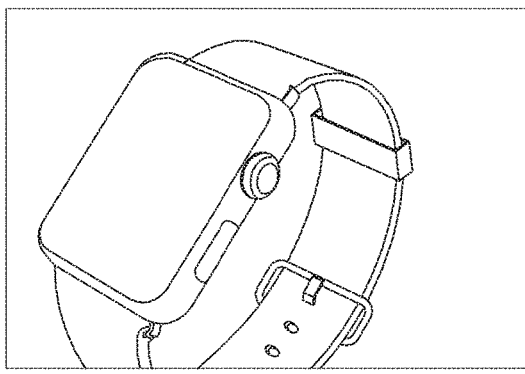
Figure 11D:
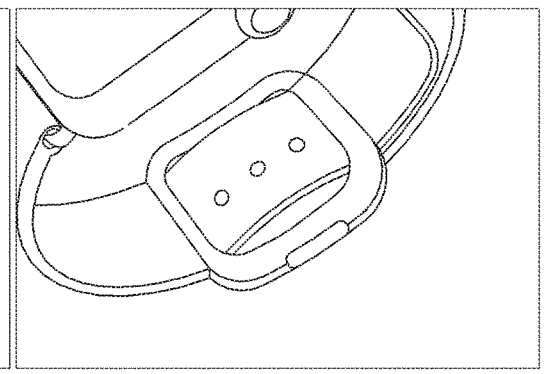
Figure 11E:
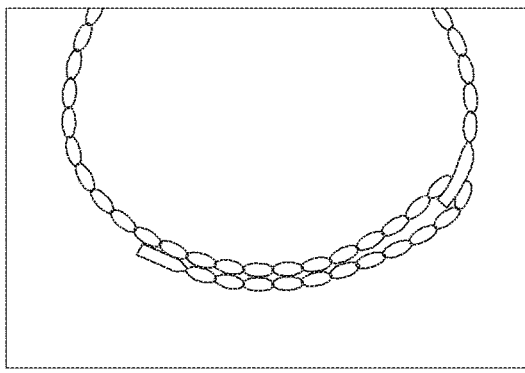
Figure 11F:
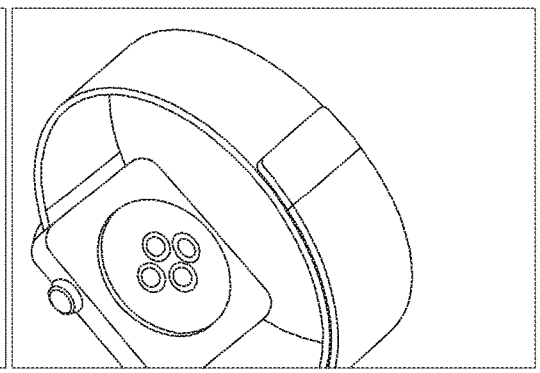

Further, there has been described an example in which the first and second strap portions 100 and 200 are separated from each other or are formed as a single body by the adapter portion or bezel portion according to an embodiment of the present disclosure. However, as shown in FIG. 8, the first strap portion 100 and the second strap portion 200 may be provided in a one-band type. The term "one-band type" means that the first strap portion 100 and the second strap portion 200 are formed to be connected with each other without separation with respect to the body portion 11. When the first and second strap portions 100 and 200 are formed in the one-band type, the body portion 11 is seated near a central portion of the first and second strap portions 100 and 200, and the first and second strap portions 100 and 200 may be provided to be elastic or adjusted in length, so that the first and second strap portions 100 and 200 may be worn on the user's body.

As described above, when the first and second strap portions 100 and 200 are formed in the one-band type, the coupling portion 12 provided in the body portion 11 may have a through opening 12e that allows the first strap portion 100 or second strap portion 200 to pass therethrough and to be coupled with both ends of the body portion 11. The first strap portion 100 or the second strap portion 200 may pass through the through opening 12e provided in both ends of the body portion 11 to be coupled with the body portion 11 (refer to FIGS. 8 and 9). Further, the second strap portion 200 is configured to be electrically connected with the body portion 11, and in this case, the body portion 11 may thus have a body terminal portion 11a, which is to be described below, as a portion contacting the body portion 11 between the through openings 13e at both sides thereof, and the second strap portion 200 may have the connecting portion 30 that is described below.

Further, although not shown, as a configuration of the coupling portion for coupling the body portion 11 with the first strap portion 100 or the second strap portion 200, a hook portion and a hooked portion hung to the hook portion may be provided. For example, the body portion 11 may have a hooked portion, and the first strap portion 100 or the second strap portion 200 may have a hook portion that is hung to the hooked portion to make a coupling or release the coupling. As the hook portion is hung to the hooked portion or hooking is released, the first strap portion 100 or the second strap portion 200 may be coupled with the body portion 11 or may be disconnected from the body portion 11. Further, when the structure, such as the hooked portion or hook portion, is provided, e.g., a releasing button with which the coupling therebetween may be released may be provided in the body portion 11. As the releasing button is pressed or works, the coupling between the hook portion and the hooked portion may be released, thus disconnecting the first strap portion 100 or second strap portion 200 from the body portion 11.

The body portion 11 may have a body terminal portion 11a (refer to FIGS. 2 and 12) that may be electrically connected with the second strap portion 200 as described below. The body terminal portion 11a may be provided at various positions depending on the configuration, structure, or shape of the second strap portion 200. For example, when the first strap portion 100 or the second strap portion 200 is coupled with the body portion 11 in an adapter type, the body terminal portion 11a may be provided on a surface facing the adapter 300, specifically, a lower surface or side surface of the body portion 11 (refer to FIG. 14). Unlike this, when the first strap portion 100 or the second strap portion 200 is coupled with the body portion 11 through a spring pin type connecting member 400, such as a connecting pin or fixing pin, the body terminal portion 11a may be provided on a surface contacting the spring pin connecting member 400 (refer to FIG. 24). Further, when the first strap portion 100 or the second strap portion 200 is coupled with the body portion 11 through a pogo pin-type connecting member 500, the body terminal portion 11a may be provided on a surface where the second strap portion 200 faces the body portion 11.

FIGS. 10A to 10F and FIGS. 11A to 11F are views illustrating diverse shapes, structures, and materials of a first strap portion or a second strap portion in a wearable device according to an embodiment of the present disclosure.

Referring to FIGS. 10A to 10F and FIGS. 11A to 11F (together with FIGS. 1 and 2), the first strap portion 100 may be a normal connecting band equipped with no function and may be detachably coupled to the body portion 11. The first strap portion 100 may be provided to allow the body portion 11 to be worn on the user's body.

The first strap portion 100 may be formed of at least one material of a metal (a), leather (b), silicone (c), urethane (d), ceramic, and fabric (e) or of at least one material of a metal (f) mixed with a mineral powder, such as tourmaline, ceramic, jade, germanium, leather, silicone, urethane, ceramic, fabric, and the like.

The first strap portion 100 may be provided to have the same structure or shape as the second strap portion 200 to be described below or may have a different structure or shape from the second strap portion 200. However, the shape or structure in which the first strap portion 100 and the second strap portion 200 are coupled with the body portion 11 may remain the same.

The first strap portion 100 may include a band 110 for fixing and a band 120 for adjustment. Further, the band 120 for adjustment and the band 110 for fixing of the first strap portion 100 may be provided as an integral strap (denoting the above-described 'one-band type') in which the connecting parts of the band 120 for adjustment and the band 110 for fixing are connected with each other without separation. When the first strap portion 100 is provided as an integral strap in one piece, first ends of the band 110 for fixing and the band 120 for adjustment may be connected with the body portion 11 or the adapter portion 300 or spring pin connecting member 400 that connects the body portion 11. Further, second ends of the band 110 for fixing and the band 120 for adjustment may have a coupling structure that enables the adjustment of the length of the band. By contrast, the band 110 for fixing and the band 120 for adjustment may be provided as separable straps having separated bodies in which their respective first ends and second ends are separated and coupled with each other.

Figure 12:
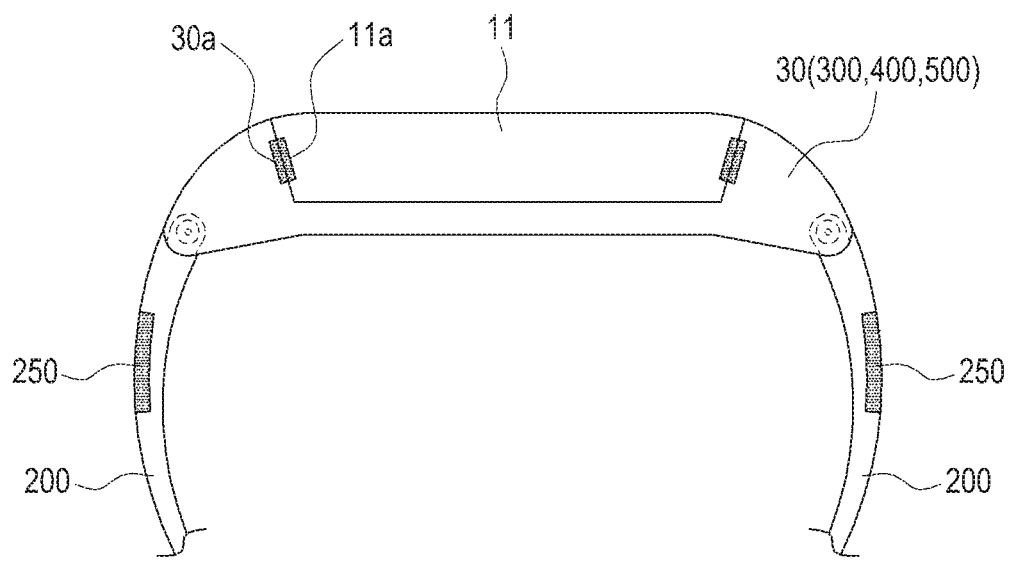
FIG. 12 is a view schematically illustrating a body portion having a second strap portion in a wearable device according to an embodiment of the present disclosure.
Figure 13:
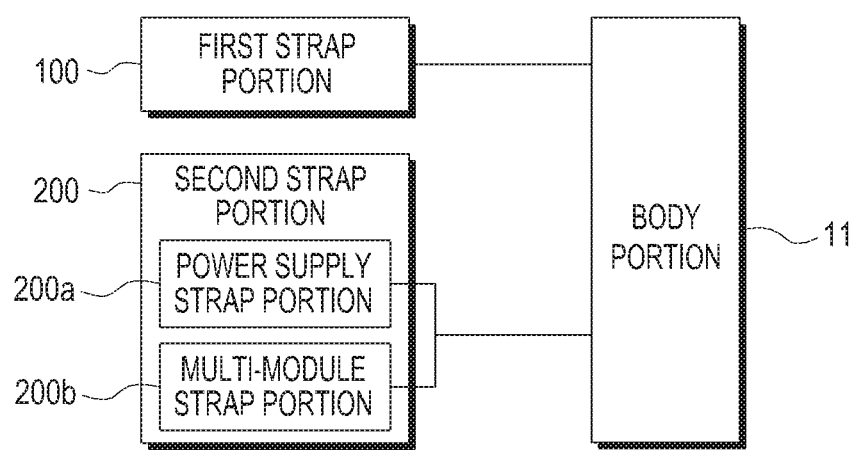
FIG. 13 is a block diagram schematically illustrating a coupling between a body portion and a first or second strap portion in a wearable device according to an embodiment of the present disclosure.

FIG. 12 is a view schematically illustrating a body portion having a second strap portion in a wearable device according to an embodiment of the present disclosure. FIG. 13 is a block diagram schematically illustrating a coupling of a first strap portion or a second strap portion to a body portion in a wearable device according to an embodiment of the present disclosure.

Referring to FIGS. 12 and 13, the second strap portion 200 is provided in the body portion 11 and has at least one function. The second strap portion 200 may be provided to be exchanged with the first strap portion 100. The second strap portion 200 may be electrically connected with the body portion 11. Further, the second strap portion 200 may have at least one member 250 allowing a signal generated from the members 250 to be supplied to the body portion 11 when the second strap portion 200 is coupled with the body portion 11.

The member 250 may be provided as at least one of modules that supplies power to the body portion 11, provides the body portion 11 with various body information, specifically information, such as the electrocardiogram (ECG), electromyogram, blood pressure, and heart rate of the user wearing the wearable device, or provides multiple functions to the body portion 11. For example, when the member 250 has a configuration that has a plurality of electrodes and a module connected thereto to detect bio information, the member 250 may measure body information, such as the user's electromyogram, electroencephalogram, blood pressure, heart rate, and the like. Further, when the member 250 is provided as a detection sensor, such as an acceleration sensor, a humidity sensor, a temperature sensor, and the like, the member 250 may provide information related to the user's ambient environment, specifically information indicating that the user is exercising or sweating, or the user's body temperature. Alternatively, the member 250 may have a configuration that may provide multiple functions, such as a speaker device, a camera module, a light emitting diode (LED), an antenna module, a haptic module, and the like. Accordingly, when the member 250 is a speaker module, a sound generated from the body portion 11 may be transferred through the speaker module mounted in the second strap portion 200. Further, when the member 250 is configured as a haptic module, when a signal is received by the body portion 11 or data is received or sent, a haptic sensation may be provided to the user's body through the haptic module provided in the second strap portion 200. As described above, the second strap portion 200 may be provided a power supply strap portion 200a and a multi-module strap portion 200b depending on the member 250 provided in the second strap portion 200. The power supply strap portion 200a is a connecting band that is provided to allow the member 250 to recharge the battery of the body portion 11 or to function as an additional battery that may provide power to the body portion 11 in addition to the battery provided in the body portion 11. Accordingly, when the power supply strap portion 200a is connected with the body portion 11, the member 250 may be connected to supply power to the body portion 11 or to supply power to the body portion 11 as a battery separate from the battery provided in the body portion 11.

As described above, when the second strap portion 200 is provided as the power supply strap portion 200a, the member 250 may include at least one of a wireless battery recharge module, an energy harvesting module, an automatic recharge module, and the like. Although an example has been described in which the power supply strap portion 200a is at least one of a wireless recharge module, an energy harvesting module, an automatic recharge module, a battery, and the like, according to the present disclosure, various changes in configuration may be made to the member 250 as long as the configuration may supply power to the battery of the body portion 11.

The multi-module strap portion 200b is a connecting band provided to allow the member 250 to provide various multiple functions to the body portion 11. Accordingly, when the multi-module strap portion 200b is connected with the body portion 11, the member 250 is electrically connected with the body portion 11, and accordingly, the member 250 is first powered by the body portion 11. The member 250 is powered by the body portion 11 and is turned off to operate. When the member 250 turns on, the member 250 is implemented in a standby mode to allow the user to run a function of the member 250, e.g., a haptic function, a speaker function, a camera module function, and the like, and the body portion 11 may be executed to run the function of the member 250 in the standby mode of the member 250 through, e.g., the user settings.

As described above, when the second strap portion 200 is provided as the multi-module strap portion 200b, the member 250 may be configured of at least one of a body information detection module, an automatic contacting module, a light emission module, a global positioning system (GPS) module, a camera module, a speaker module, a haptic module, a put-on-body detection module, and the like.

Although the power supply strap portion 200a or multi-module strap portion 200b has been described as an example of the member 250 according to an embodiment of the present disclosure, embodiments of the present disclosure are not limited thereto. For example, other various modules may be mounted in the member 250 depending on the function of the second strap portion 200 or the user's needs. For example, the member 250 may be provided as a screen portion that may display a screen separately from the display unit 11b provided in the body portion 11, may have a module that enables communication with an external device or connection to the external device, or may be provided, like a projector, to project the screen displayed on the display unit 11b of the body portion 11 to the back of the user's hand or an external screen. As such, various changes in type may be made to the member 250 mounted in the second strap portion 200 depending on the user's needs or user environment.

The second strap portion 200 may be formed of at least one material of a metal, leather, silicone, urethane, ceramic, and fabric or of at least one material of a metal mixed with a mineral powder, such as tourmaline, ceramic, jade, germanium, leather, silicone, urethane, ceramic, fabric, and the like (refer to FIGS. 10A to 10F and FIGS. 11A to 11F).

Similar to the above-mentioned first strap portion 100, the second strap portion 200 may include a band 210 for fixing and a band 220 for adjustment. The band 220 for adjustment and the band 210 for fixing of the second strap portion 200 may be provided as an integral strap in which the connecting parts of the band 220 for adjustment and the band 210 for fixing are connected with each other without separation. When the second strap portion 200 is provided as an integral strap in one piece, first ends of the band 210 for fixing and the band 220 for adjustment may be connected with the body portion 11 or the adapter that connects the body portion 11. Further, second ends of the band 210 for fixing and the band 220 for adjustment may have a coupling structure that enables the adjustment of the length of the band. By contrast, the band 210 for fixing and the band 220 for adjustment may be provided as separable straps having separated bodies in which their respective first ends and second ends are separated and coupled with each other. The band 220 for adjustment may be coupled with the band 210 for fixing through a structure, such as a separated buckle or a continuous integral buckle, through a magnetic attracting force, or through a hooked ring or hooked member 250 (refer to FIGS. 3 to 11F).

As described above, the first strap portion 100 is a normal connecting band, and the second strap portion 200 is a functional connecting band providing at least one function. The user may couple the first strap portion 100, which is a normal connecting band, to the body portion 11 depending on his needs, or may couple the second strap portion 200, which is a functional connecting band, to the body portion 11 (refer to FIGS. 1 and 2).

The connecting portion 30 may be provided to couple the body portion 11 with the first strap portion 100 or the second strap portion 200 or to electrically connect the body portion 11 with the second strap portion 200. The connecting portion 30 may include a first connecting portion 31 and a second connecting portion 32. The first connecting portion 31 may be provided to couple the first strap portion 100 to the body portion 11. The second connecting portion 32 may be provided to couple the second strap portion 200 to the body portion 11 (refer to FIGS. 1 and 2).

A detachable coupling structure between the first strap portion 100 and the second strap portion 200, a connecting structure between the second strap portion 200 and the body portion 11, a water proof structure, user environment settings according to compatible attachment and detachment of the first strap portion 100 and the second strap portion 200, and a short circuit preventing structure according to compatible attachment and detachment of the first strap portion 100 and the second strap portion 200 are now described one by one with reference to FIGS. 13 to 39. Further, user environment settings between the body portion 11 and the second strap portion 200 depending on the member 250 provided in the second strap portion 200 may be described one by one.

Figure 14:
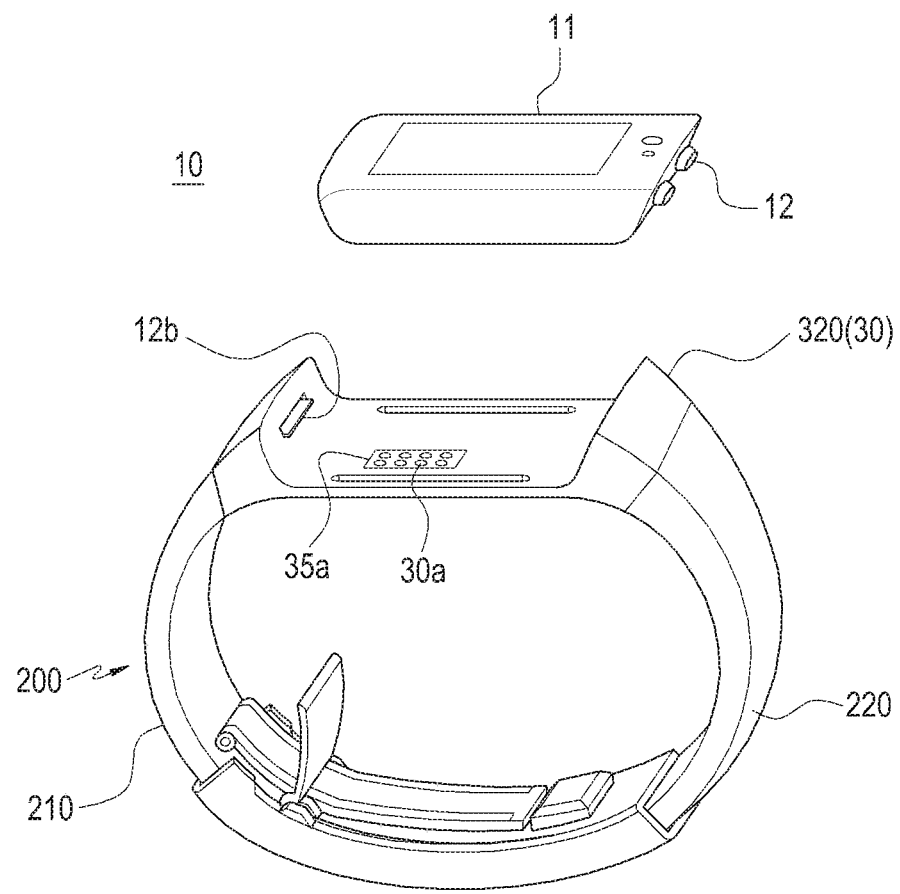
FIG. 14 is a view schematically illustrating a coupling between a body portion and a second strap portion through an adapter according to a first embodiment in a wearable device according to an embodiment of the present disclosure.
Figure 15:
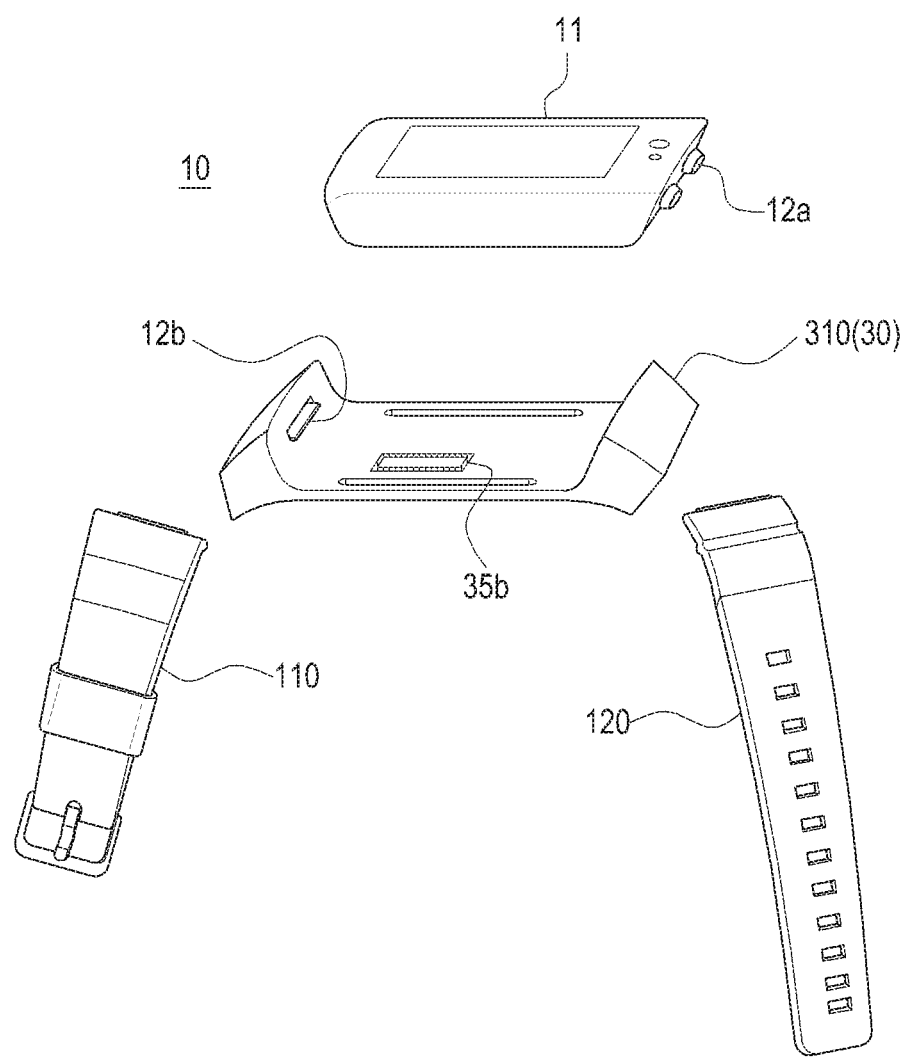
FIG. 15 is a view schematically illustrating a coupling between a body portion and a first strap portion through an adapter according to the first embodiment in a wearable device according to an embodiment of the present disclosure.

FIG. 14 is a view schematically illustrating a coupling between a body portion and a second strap portion through an adapter portion according to a first embodiment in a wearable device according to an embodiment of the present disclosure. FIG. 15 is a view schematically illustrating a coupling between a body portion and a first strap portion through an adapter portion according to the first embodiment in a wearable device according to an embodiment of the present disclosure.

Referring to FIGS. 14 and 15, the second strap portion 200 having the functional member 250 may be provided as a single-piece strap or separable straps. The second strap portion 200 may have a connecting portion 30 (hereinafter, the second connecting portion 32) connected with the body portion 11. According to an embodiment of the present disclosure, the second connecting portion 32 may be provided as an adapter portion 320 (hereinafter, a second adapter portion 320) to allow the body portion 11 to be seated while surrounding a rear surface of the body portion 11. The second adapter portion 320 may be provided like a single body while fixed to the second strap portion 200, specifically, an end of the band 210 for fixing and an end of the band 220 for adjustment. By contrast, the second adapter portion 320 may be provided in a separated type to be detachable to the second strap portion 200, specifically, an end of the band 210 for fixing and an end of the band 220 for adjustment (refer to FIGS. 1, 20, and 22A and 22B).

As described above, the second adapter portion 320 may be provided to be seated while surrounding the rear surface of the body portion 11, facing the rear surface of the body portion 11. In a surface of the second adapter portion 320, specifically, a surface facing the body portion 11, may be provided a connection terminal portion 30a that may be electrically connected with the body terminal portion 11a. According to an embodiment of the present disclosure, the body terminal portion 11a is described as provided in a surface of the body portion 11, e.g., a rear surface of the body portion 11. Accordingly, the connection terminal portion 30a may be provided in an upper surface of the second adapter portion 320 (refer to FIG. 16 as well).

The first strap portion 100 may be provided as a single-piece strap or separable straps like the second strap portion 200. The first strap portion 100 may have a connecting portion 30 (hereinafter, a first connecting portion 31) that enables the first strap portion 100 to connect to the body portion 11. According to an embodiment of the present disclosure, the first connecting portion 31 may be provided as an adapter portion 310 (hereinafter, a first adapter portion 310) that has the same structure and shape as the above-described second connecting portion 32. The first adapter portion 310 is an intervening structure that enables the first strap portion 100 to be coupled with the body portion 11. Specifically, the first adapter portion 310 may be provided to allow the band 110 for fixing and the band 120 for adjustment of the first strap portion 100 to be coupled to both ends of the body portion 11. The first adapter portion 310, like the second adapter portion 320, may be implemented in a fixed state as a single piece, or unlike this, may be implemented to be detachably separated from the first strap portion 100.

Figure 16:
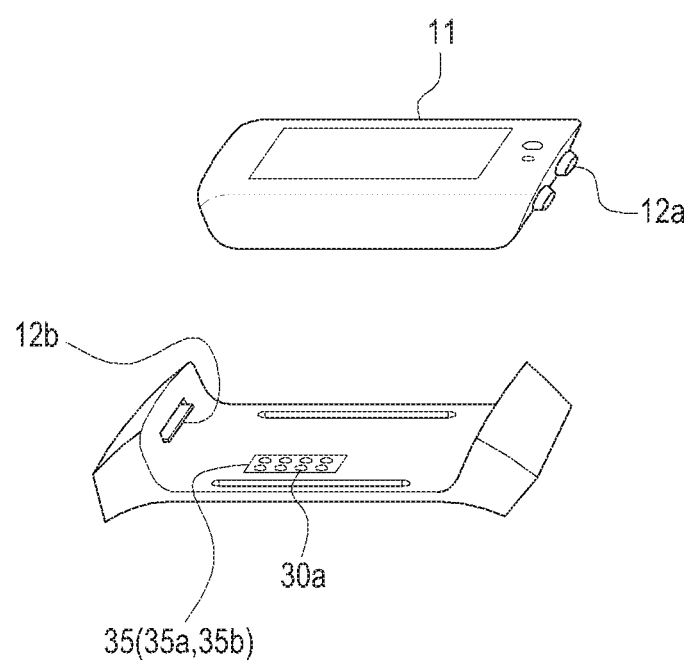
FIG. 16 is a perspective view illustrating a sealing member being provided along an edge of a first adapter portion or a second adapter portion in a wearable device according to an embodiment of the present disclosure.
Figure 17:
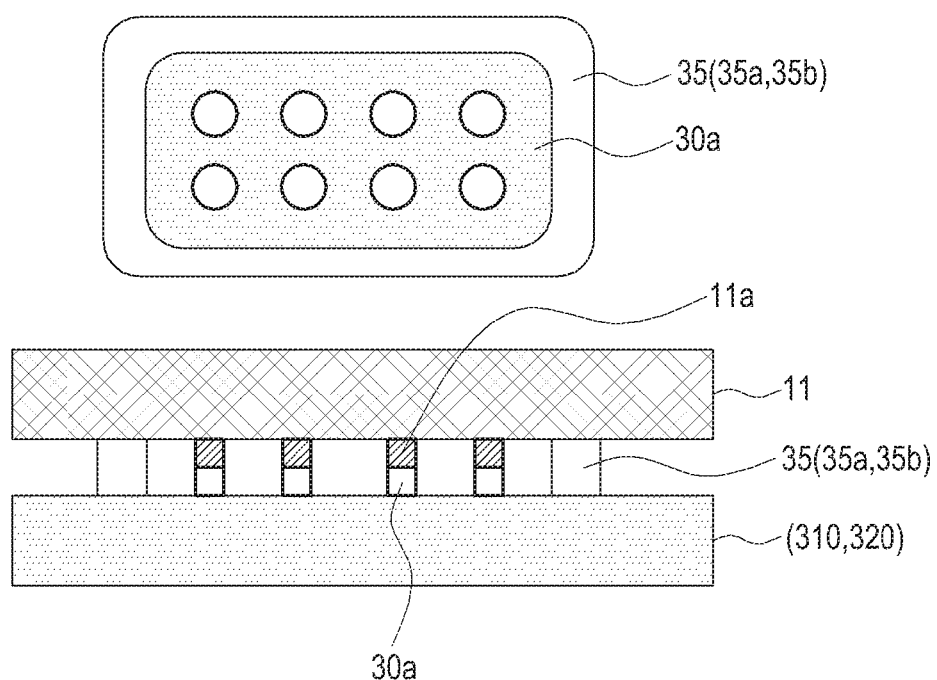
FIG. 17 is a plan view and a cross-sectional view illustrating a sealing member being provided along an edge of a first adapter portion or a second adapter portion in a wearable device according to an embodiment of the present disclosure.

FIG. 16 is a perspective view illustrating a sealing member being provided along an edge of a first adapter portion or a second adapter portion in a wearable device according to an embodiment of the present disclosure. FIG. 17 includes a plan view and a cross-sectional view illustrating a sealing member being provided along an edge of a first adapter portion or a second adapter portion in a wearable device according to an embodiment of the present disclosure.

Referring to FIGS. 16 and 17, a sealing member 35 may be provided between the body portion 11 and the first adapter portion 310 or between the body portion 11 and the second adapter portion 320 to provide tight contact and sealing between the body terminal portion 11a and the connection terminal portion 30a or to seal an area around the periphery of the body terminal portion 11a. The sealing member 35 may be provided while seated at the periphery of the body terminal portion 11a or the periphery of the connection terminal portion 30a. The sealing member 35 may be provided to include at least one material of rubber, synthetic rubber, silicone, urethane, and the like. The sealing member 35 may be formed of an elastic material as described above, and may thus be brought in tight contact as the body portion 11 is coupled with the second adapter portion 320.

Figures 18A, 18B:
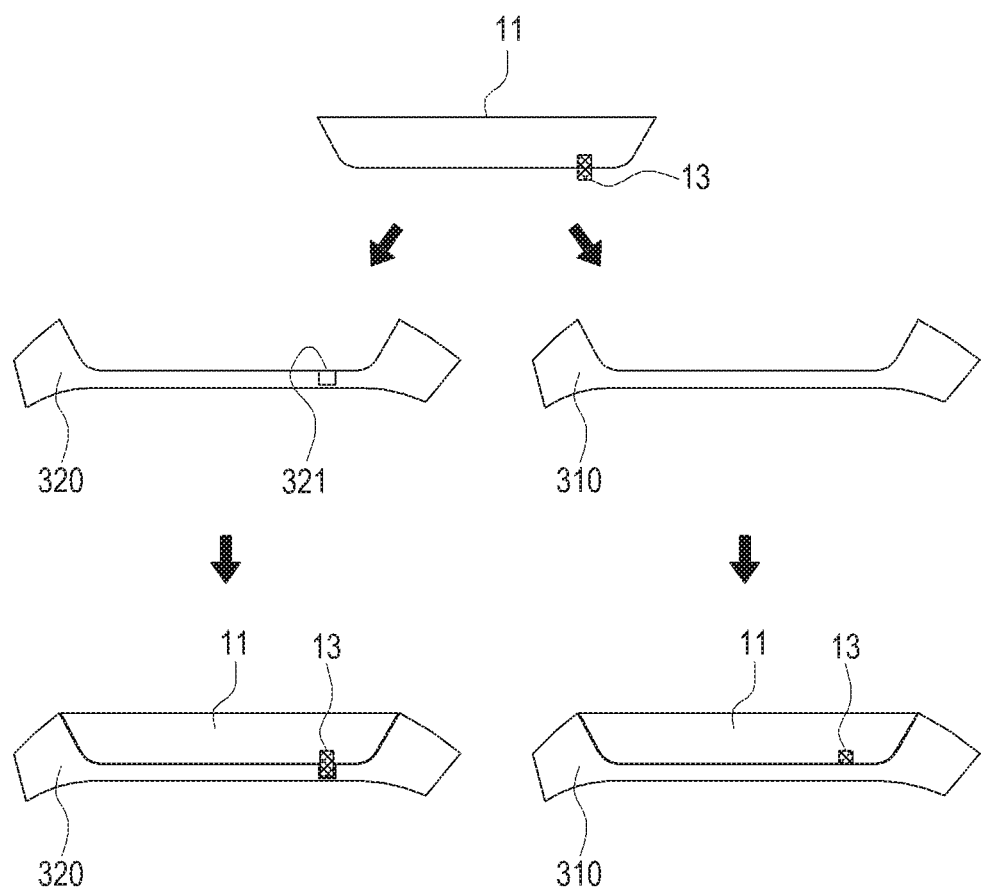
FIGS. 18A and 18B are views illustrating a body portion having a detecting unit in a wearable device according to an embodiment of the present disclosure.

FIGS. 18A and 18B are views illustrating a body portion having a detecting unit in a wearable device according to an embodiment of the present disclosure.

Figures 22A, 22B:
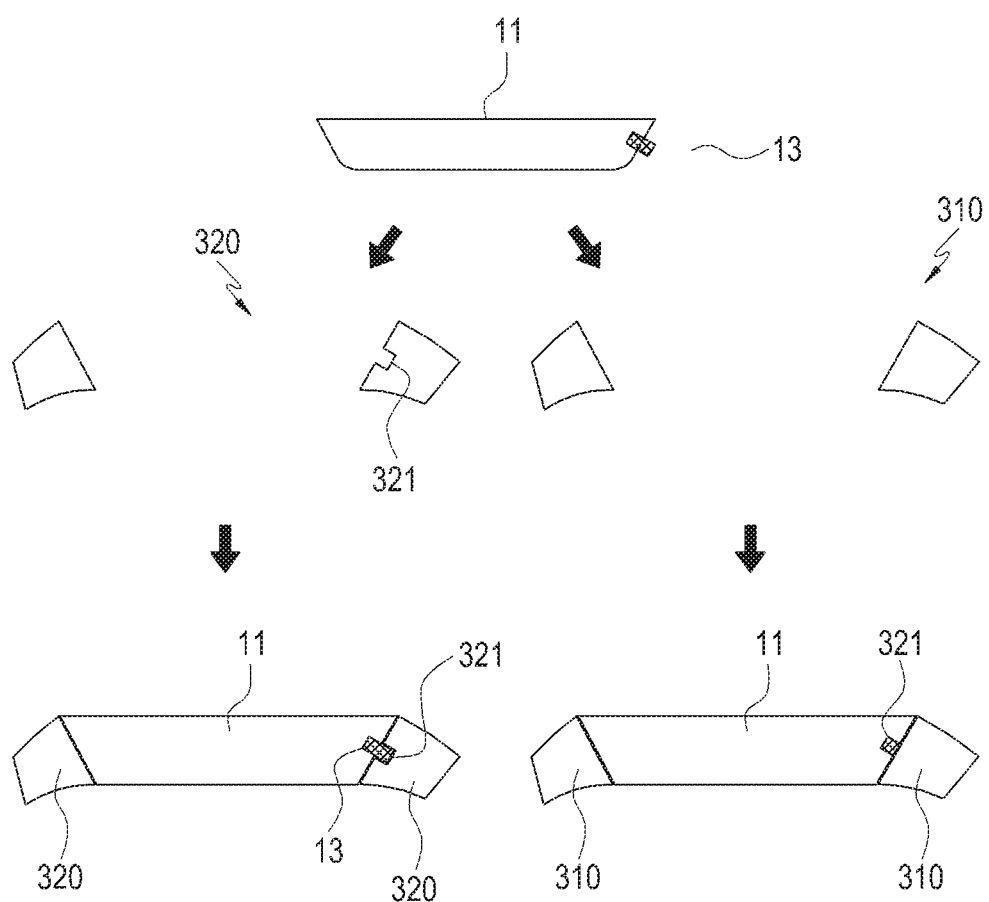
FIGS. 22A and 22B are views illustrating a body portion having a detecting unit in a wearable device according to an embodiment of the present disclosure.

Referring to FIGS. 18A and 18B, the body portion 11 may include a detecting unit 13 that may detect attachment or detachment of the first adapter portion 310 or the second adapter portion 320. The detecting unit 13 may be provided to detect the attachment or detachment of the second strap portion 200 or to detect the attachment or detachment of at least one of the power supply strap portion 200a or the multi-module strap portion 200b. The detecting unit 13 may be positioned on a coupled surface between the body portion 11 and the adapter portion 310 and 320. According to an embodiment of the present disclosure, an example is described in which the detecting unit 13 is provided at a corresponding position on a rear surface of the body portion 11 and an upper surface of the adapter portion 310 and 320. However, the position of the detecting unit 13 is not limited thereto. For example, as shown in FIGS. 22A and 22B to be described below, the detecting unit 13 may be provided between an end of the body portion 11 and the adapter portion 310 and 320.

The detecting unit 13 may be operated to determine when the first strap portion 100 or the second strap portion 200 is coupled to the body portion 11, and thus, the detecting unit 13 is pressed or depressed, or whether an electrical signal is applied or when a detecting signal is applied. Accordingly, a current flowing as the first strap portion 100 is coupled to the body portion 11 and thus the body terminal portion 11*a* contacts the first strap portion 100 may be prevented from being applied to the first strap portion 100 while preventing a short circuit from occurring in the body portion 11.

The detecting unit 13 may be provided as at least any one of a mechanical button switch, a pogo terminal portion, a pressure sensor, a hall sensor, and the like. For example, when the detecting unit 13 is provided to be pressed as the first strap portion 100 is coupled, the detecting unit 13 may be provided not to be pressed when the second strap portion 200 is coupled. Further, when the detecting unit 13 is provided so that when the first strap portion 100 is coupled, an electrical signal or detecting signal is applied to the detecting unit 13, the detecting unit 13 may be provided so that when the second strap portion 200 is coupled, no electrical signal or detecting signal is applied to the detecting unit 13. When the coupling of the second strap portion 200 is recognized by the body portion 11 as the detecting unit 13 is operated, the function of the member 250 may be controlled to be operated through the body portion 11.

According to an embodiment of the present disclosure, an example in which the detecting unit 13 is provided as a mechanical button switch is described. For example, the detecting unit 13 provided as a mechanical button switch may be projectingly formed on a rear surface of the body portion 11. Further, although no disclosure is provided as to a structure configured to the mechanical button switch in the first adapter portion 310, an opening 321 where the mechanical button switch is seated may be formed on a surface of the second adapter portion 320. Accordingly, when the first adapter portion 310 is coupled with the body portion 11, the mechanical button switch provided in the rear surface of the body portion 11 is pressed, and the body portion 11 may be operated to restrict application of a current to the body terminal portion 13*a*. Unlike this, when the second adapter portion 320 is coupled with the body portion 11, the mechanical button switch provided in the rear surface of the body portion 11 may be pulled into the opening 321. Accordingly, the body portion 11 may apply current to the body terminal portion 13*a*, and the body terminal portion 13*a* is electrically connected with the connection terminal portion 30*a*, enabling signal input. When a signal from the member 250 is applied to the body portion 11, the battery may be recharged or power may be supplied to the member 250 depending on the type of the member 250 provided in the second strap portion 200, and may be electrically connected with the member 250, allowing itself to be operated in a standby mode in which user settings may be executed according to the member 250.

Figure 19:
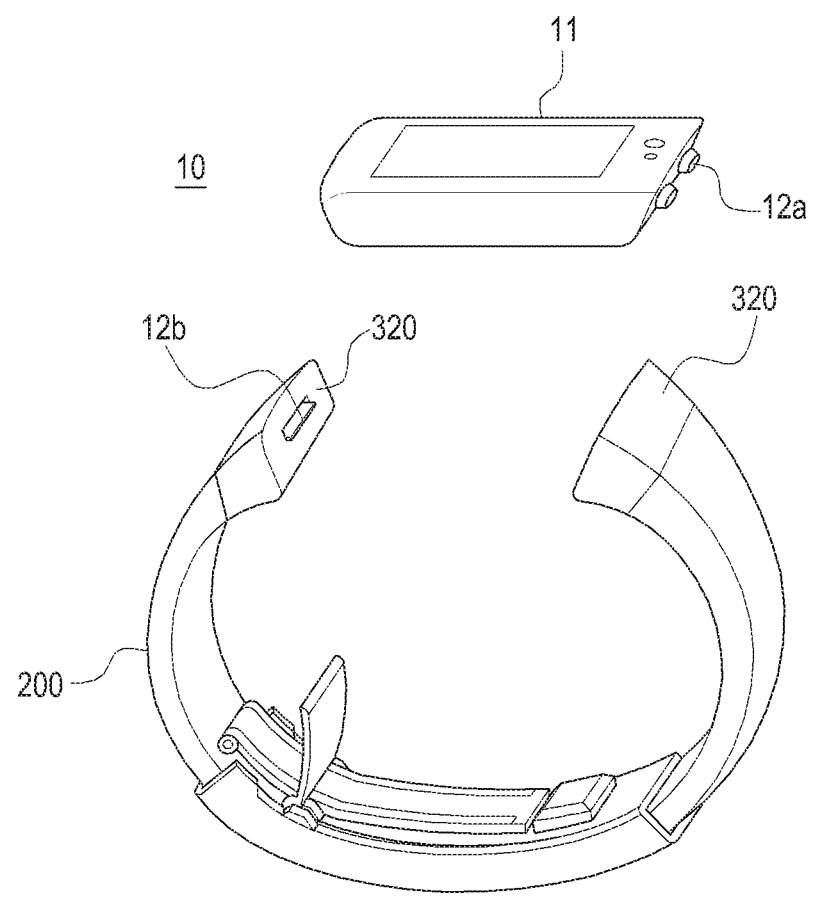
FIG. 19 is a view schematically illustrating a coupling between a body portion and a second strap portion through an adapter according to a second embodiment in a wearable device according to an embodiment of the present disclosure.
Figure 20:
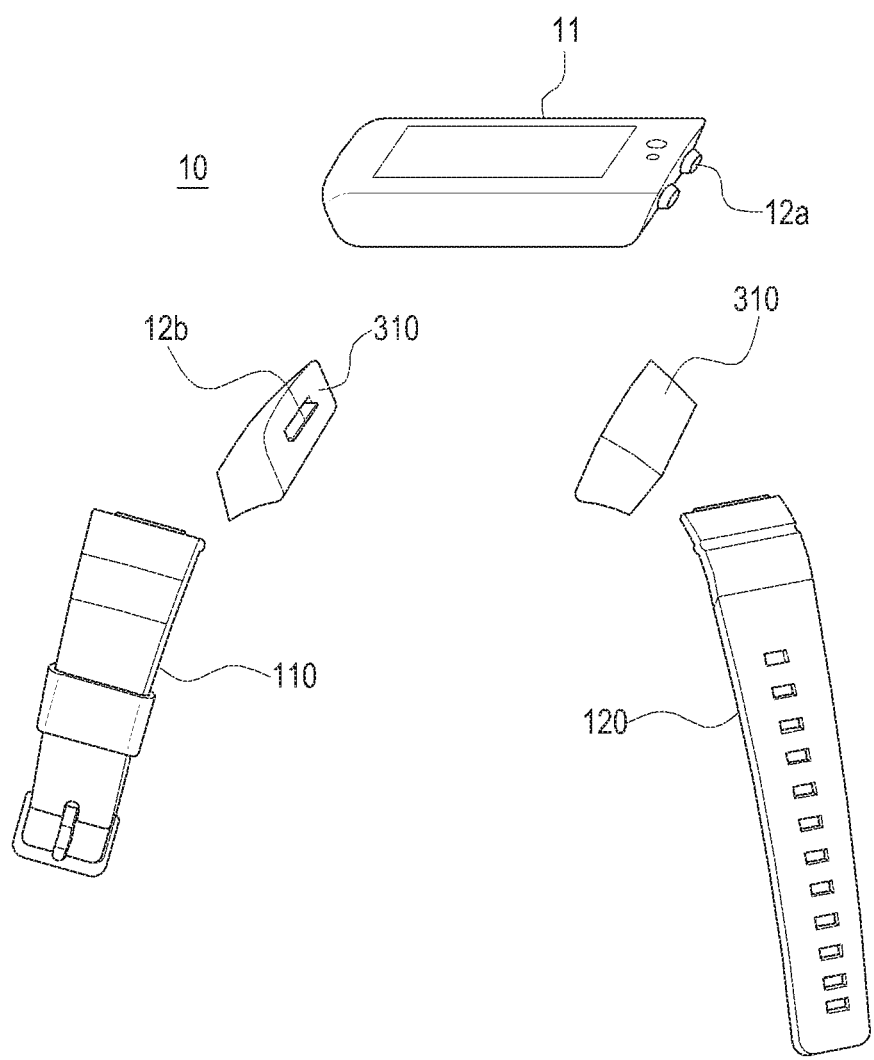
FIG. 20 is a view schematically illustrating a coupling between a body portion and a first strap portion through an adapter according to the second embodiment in a wearable device according to an embodiment of the present disclosure.

FIG. 19 is a view schematically illustrating a coupling between a body portion and a second strap portion through an adapter portion according to a second embodiment in a wearable device according to an embodiment of the present disclosure. FIG. 20 is a view schematically illustrating a coupling between a body portion and a first strap portion through an adapter portion according to the second embodiment in a wearable device according to an embodiment of the present disclosure.

Referring to FIGS. 19 and 20, although the above-described adapter portion 300 according to the first embodiment of the present disclosure is provided in shape to connect the band 110 and 210 for fixing with the band 120 and 220 for adjustment, the adapter portion 300 according to the second embodiment of the present disclosure is provided at each of ends of the band 110 and 210 for fixing and the band 120 and 220 for adjustment. Specifically, a second adapter portion 320 may be first described for electrically connecting the second strap portion 200 with the body portion 11. The second adapter portion 320 may be provided at each of the ends of the band 210 for fixing and the band 220 for adjustment. The second adapter portion 320 provided at each of the band 220 for adjustment and the band 210 for fixing may be provided to be coupled with each of first and second ends of the body portion 11. At least any one of the second adapter portions 320 respectively connected to the band 210 for fixing and the band 220 for adjustment may have a connection terminal portion 30*a* electrically connected with the body terminal portion 11*a* provided at both ends of the body portion 11.

The second adapter portion 320 may be fixedly provided as a single piece at each of the ends of the band 210 for fixing and the band 220 for adjustment. Unlike this, the second adapter portions 320 respectively provided at the ends of the band 210 for fixing and the band 220 for adjustment may be provided to be detachably separated from the end of the band 210 for fixing and the end of the band 220 for adjustment.

Figure 21:
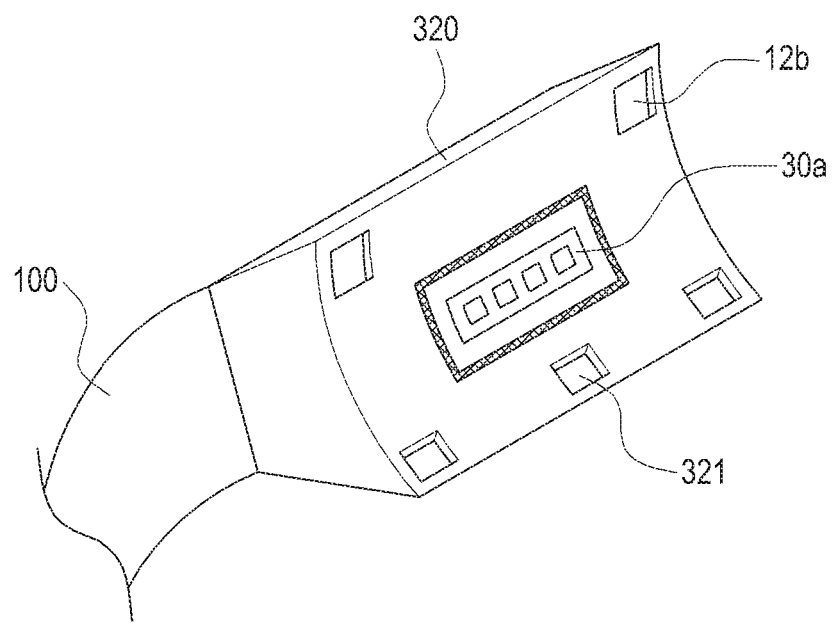
FIG. 21 is a perspective view illustrating a first adapter portion or a second adapter portion in a wearable device according to an embodiment of the present disclosure.

FIG. 21 is a perspective view illustrating a first adapter portion or a second adapter portion in a wearable device according to an embodiment of the present disclosure.

Referring to FIG. 21, a sealing member 35 may be provided between the body portion 11 and the first adapter portion 310 or between the body portion 11 and the second adapter portion 320 to provide tight contact and sealing between the body terminal portion 11*a* and the connection terminal portion 30*a* or to seal an area around the periphery of the body terminal portion 11*a*. The sealing member 35 may be provided while seated at the periphery of the body terminal portion 11*a* or the periphery of the connection terminal portion 30*a*. The sealing member 35 may be provided to include at least one material of rubber, synthetic rubber, silicone, urethane, and the like. The sealing member 35 may be formed of an elastic material as described above, and may thus be brought in tight contact as the body portion 11 is coupled with the second adapter portion 320.

FIG. 22 is a view illustrating a body portion having a detecting unit in a wearable device according to an embodiment of the present disclosure.

Referring to FIG. 22, the body portion 11 may include a detecting unit 13 that may detect attachment or detachment of the first adapter portion 310 or the second adapter portion 320. According to the present disclosure, the adapter portion 310 and 320 has a structure to be coupled to both ends of the body portion 11, and thus, the detecting unit 13 may be provided in a coupled surface between at least one of the two opposite ends of the body portion 11 and the adapter portion 310 and 320. The detecting unit 13 is the same as that described above in connection with FIG. 18, and the above description may apply.

Figure 23:
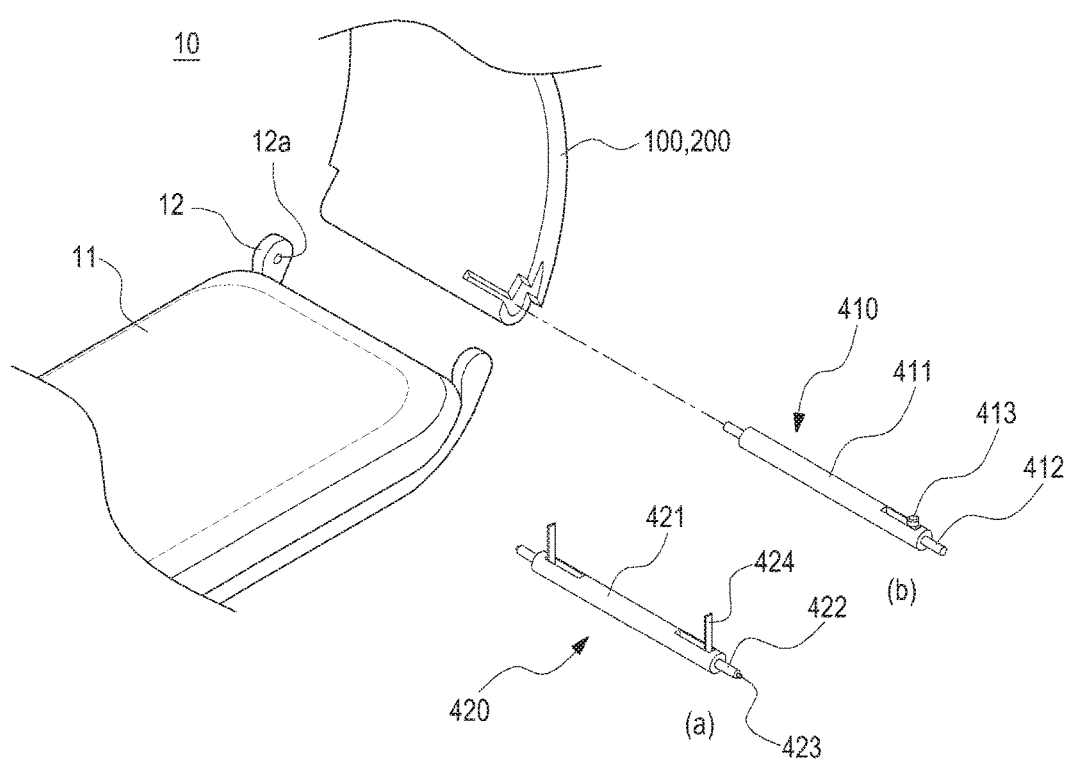
FIG. 23 is a view illustrating a connecting portion according to the second embodiment in a wearable device according to an embodiment of the present disclosure.

FIG. 23 is a view illustrating a connecting portion according to the second embodiment in a wearable device according to an embodiment of the present disclosure.

Referring to FIG. 23, the connecting portion 30 (hereinafter, denoted with the reference numeral '400') according to an embodiment of the present disclosure may include a first connecting module 410 and a second connecting module 420. According to the second embodiment of the present disclosure, an example in which the first connecting module 410 and the second connecting module 420 are provided as spring pin-type connecting members 400 is described.

First, the first connecting module 410 disclosed in illustration (a) of FIG. 23 may be described. The first connecting module 410 may be provided between the first strap portion 100 and the body portion 11 and may detachably couple the first strap portion 100 to the body portion 11.

The first connecting module 410 may include a first pin body, a first protrusion portion 412 (functioning as the second coupling portion 12b), and a first lever portion 413.

The first pin body 411 may be provided to be pulled in between the first strap portion 100 and the body portion 11. Specifically, the first pin body 411 may be provided to be seated in the first strap portion 100 and may be provided so that both ends thereof are projected to both ends of the first strap portion 100. The first pin body 411 may be provided to be fitted into the end of the first strap portion 100, and both ends of the first pin body 411 may be provided to be projected to both sides of the first strap portion 100.

The first protrusion portion 412 may be provided to be projected from both ends of the first pin body 411, and at least one of the first protrusion portions 412 projected from both ends of the first pin body 411 may be elastically provided to be pulled in the inside of the first pin body 411.

The first lever portion 413 may be provided to be projected from the inside of the first pin body 411 to an outside of the body portion 11. Specifically, the first lever portion 413 may be provided to be projected to the outside of the coupling portion 12 and the first strap portion 100 to control the movement of at least one of the first protrusion portions 412 projecting from both ends of the first pin body 411. When the first lever portion 413 is moved, the first protrusion portion 412 connected to the first lever portion 413 may be moved to the inside of the first pin body 411. As the first protrusion portion 412 that has been seated in the coupling hole 12a is departed from the coupling hole 12a, the first protrusion portion 412 may be departed from the coupling portion 12 of the body portion 11, so that the first strap portion 100 may be detached from the body portion 11.

Figure 24:
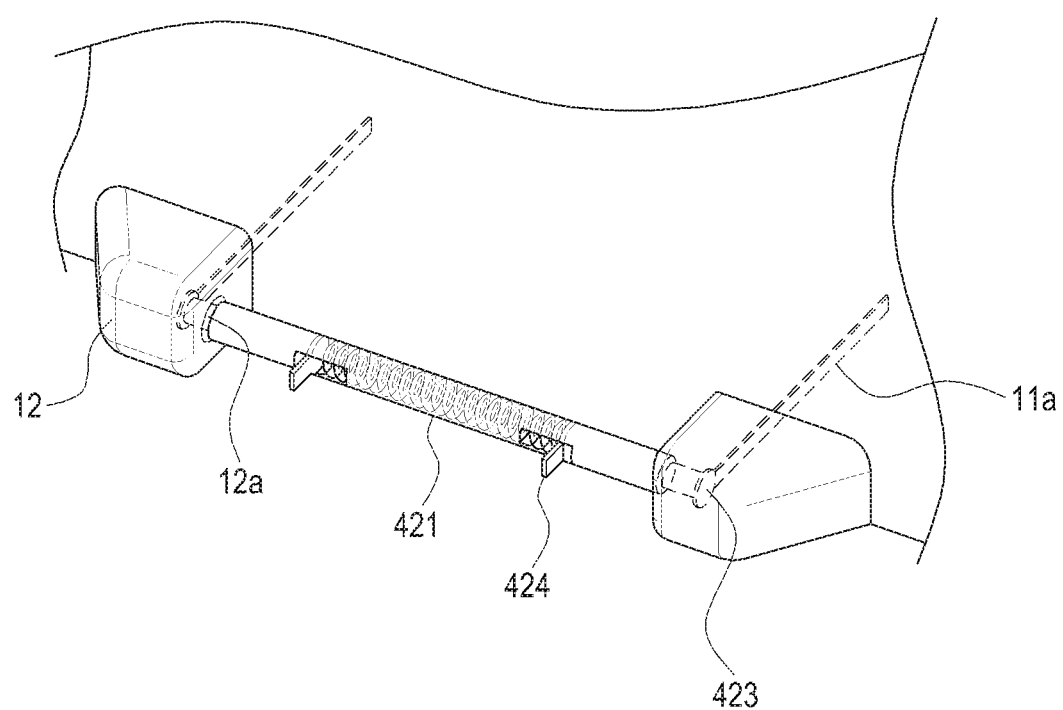
FIG. 24 is a view illustrating a second connecting module according to the second embodiment being connected to a body portion in a wearable device according to an embodiment of the present disclosure.

FIG. 24 is a view illustrating a second connecting module according to the second embodiment being connected to a body portion in a wearable device according to an embodiment of the present disclosure.

Referring to FIG. 24 (together with illustration (b) of FIG. 23), the second connecting module 420 may be provided to couple the second strap portion 200 provided to be compatible with the first strap portion 100 to the body portion 11. The second connecting module 420 may be provided to be compatible with the first connecting module 410 and may couple the second strap portion 200 to the body portion 11. Further, the second connecting module 420 may be provided to electrically connect the second strap portion 200, specifically, the member 250, to the body portion 11 to transfer a signal from the member 250 to the body portion 11. For example, the second connecting module 420 may be provided to electrically connect the body portion 11 with the second strap portion 200 while fixedly coupling the body portion 11 with the second strap portion 200.

The second connecting module 420 may include a second pin body 421, a second protrusion portion 422, a connecting pin portion 423, and a connector pin portion 424.

The second pin body 421 may be provided to be pulled in between the second strap portion 200 and the body portion 11. Specifically, the second pin body 421 may be provided to be fitted and seated in an end of the second strap portion 200 and may be provided so that both ends thereof are projected to both ends of the second strap portion 200. The second protrusion portion 422 may be provided to be projected from both ends of the second pin body 421 while projected from both sides of the second strap portion 200 when the second pin body 421 is fitted into the second strap portion 200. The second protrusion portion 422 may be provided to be fitted into the coupling holes 12a provided at both ends of the coupling portion 12 of the body portion 11 to fasten the second strap portion 200 to the body portion 11.

At least one of the second protrusion portions 422 projected from both ends of the second pin body 421 may be provided to be elastically driven into the inside of the second pin body 421.

The second connecting module 420, like the above-described first connecting module 410, may include a separate lever portion (not shown) for driving the second protrusion portion 422.

The connecting pin portion 423 may be provided in the second protrusion portion 422. The connecting pin portion 423 may be provided to be electrically connected with the body terminal portion 11a extended to the side of the coupling hole 12a of the coupling portion 12 from the inside of the body portion 11.

The connector pin portion 424 may be provided in the second pin body 421 and may be provided to be bent at the connecting pin portion 423 to be projected to the inside of the second strap portion 200. The connector pin portion 424 may be provided to be electrically connected with the connecting pin portion 423 while electrically connected with the member 250 mounted in the second strap portion 200.

Figure 25:
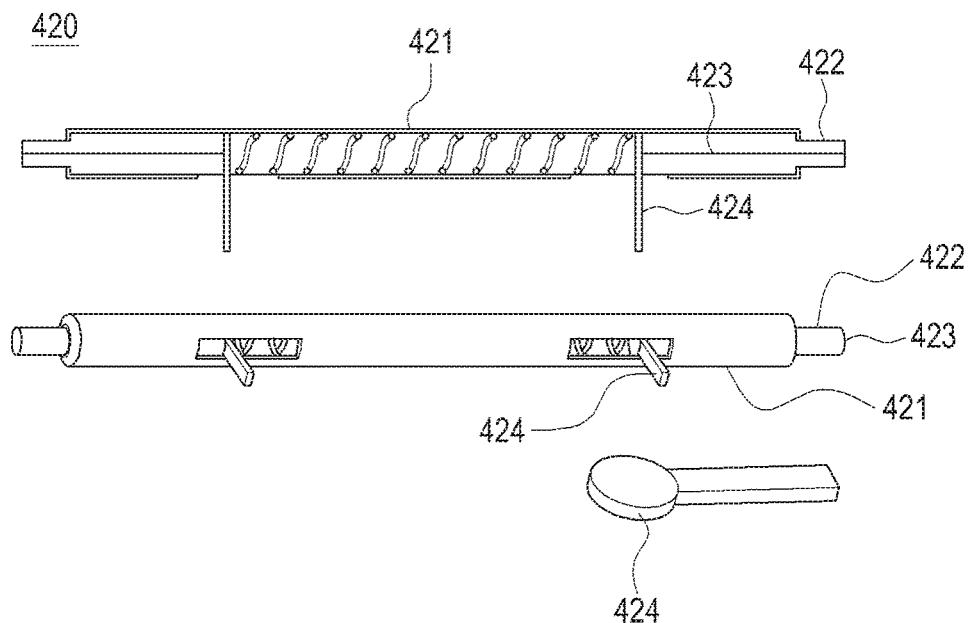
FIG. 25 is a view illustrating a two pin-type second connecting module according to the second embodiment in a wearable device according to an embodiment of the present disclosure.
Figure 26:
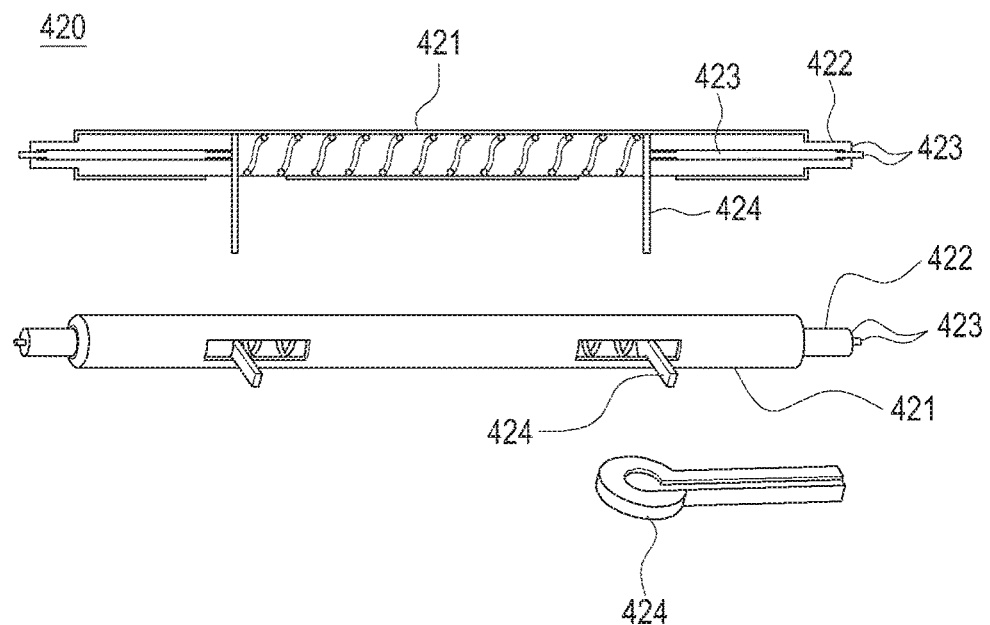
FIG. 26 is a view illustrating a four pin-type second connecting module according to the second embodiment in a wearable device according to an embodiment of the present disclosure.

FIG. 25 is a view illustrating a two pin-type second connecting module according to the second embodiment in a wearable device according to an embodiment of the present disclosure. FIG. 26 is a view illustrating a four pin-type second connecting module according to the second embodiment in a wearable device according to an embodiment of the present disclosure.

Referring to FIGS. 25 and 26, an example is described in which the connecting pin portion 423 according to an embodiment of the present disclosure is provided in at least one of a two pin type or a four pin type. Specifically, as the connecting pin portion 423 is connected in the two pin type or four pin type, a difference may arise in the member 250 provided in the second strap portion 200. For example, when the above-described second strap portion 200 is provided as the power supply strap portion 200a, the second strap portion 200 is enough to provide a signal line for transferring signals from the member 250 to the body portion 11. Accordingly, the connecting pin portion 423 and the connector pin portion 424 may be provided in the two pin type. For example, when the power supply strap portion 200a is coupled with the body portion 11, a signal for recharging, rather than data or a signal, may be transferred from the power supply strap portion 200a to the body portion 11 through the member 250, and accordingly, they may be provided in the two pin type.

Further, when the second strap portion 200 is provided as the multi-module strap portion 200b as described above, the connecting pin portion 423 and the connector pin portion 424 may be provided in the four pin type. For example, when the multi-module strap portion 200b is coupled to the body portion 11, power from the body portion 11 should be delivered to the member 250 of the multi-module strap portion 200b, and since signal values from the member 250 should be transferred to the body portion 11, they may be provided in the four pin type so that they each may be electrically connected.

Although not separately shown, the second pin body 421 and the second protrusion portion 422 may have an insulation coating layer. Further, the connecting pin portion 423 and the connecting pin portion 423 may also have an insulation coating layer at the rest except the portion where an electrical connection is formed.

Accordingly, an end of the body terminal portion 11a and an end of the connecting pin portion 423 may be electrically communicated with each other, but the other portions may be prevented from current flow, thus preventing a short circuit from in the body portion 11 or malfunctions or errors due to current leakage.

Figure 27A:
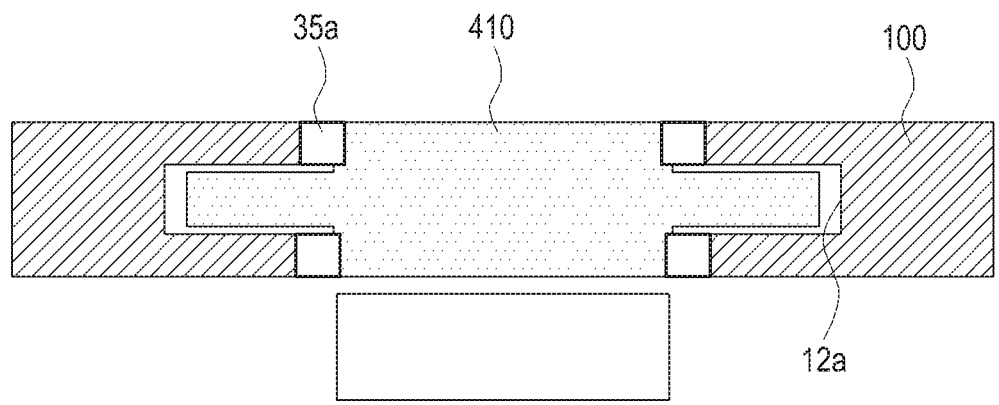
FIGS. 27A and 27B are views schematically illustrating a sealing member being provided between a body portion and a second strap portion according to the second embodiment in a wearable device according to an embodiment of the present disclosure.
Figure 27B:
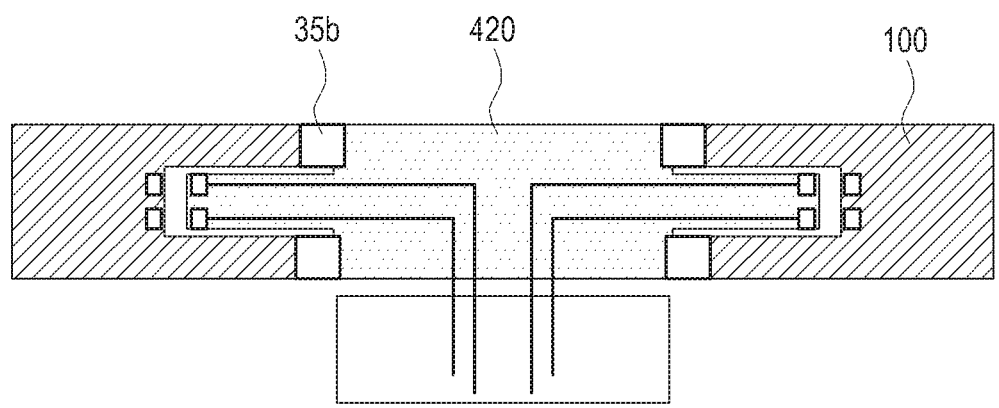

FIGS. 27A and 27B are views schematically illustrating a sealing member being provided between a body portion and a first strap portion and a second strap portion according to the second embodiment in a wearable device according to an embodiment of the present disclosure.

Referring to FIGS. 27A and 28B, a first sealing member 35a and a second sealing member 35b may be provided between the first strap portion 100 and the second strap portion 200 and the body portion 11 to seal the coupled surface between the first strap portion 100 and the body portion 11. First, the first sealing member 35a may be provided between the first connecting module 410, specifically the first pin body 411, and the coupling portion 12a of the coupling portion 12 to provide tight sealing therebetween. The first sealing member 35a may be provided in an O-ring shape.

The second sealing member 35b may be provided between the second connecting module 420, specifically the second pin body 421, and the coupling portion 12a of the coupling portion 12 to provide tight sealing therebetween. The second sealing member 35b may be provided in an O-ring shape.

The first sealing member 35a and the second sealing member 35b may be provided to include at least one material of rubber, synthetic rubber, silicone, urethane, and the like. The sealing member 35 may be formed of an elastic material as described above, and may thus be brought in tight contact as the body portion 11 is coupled with the first strap portion 100 or second adapter portion 200.

Figure 28:
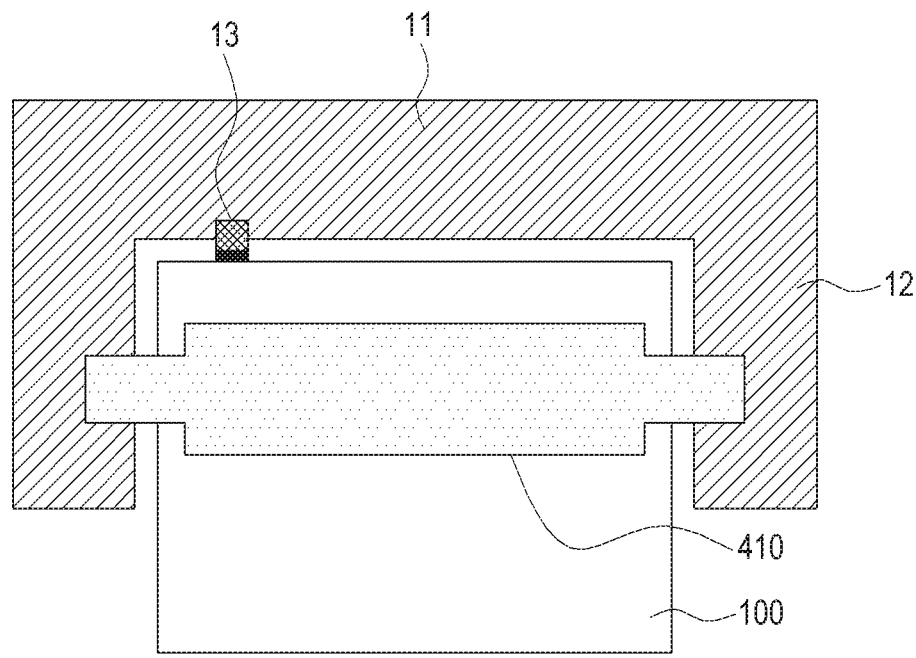
FIG. 28 is a view illustrating a first connecting module being provided in a body portion having a detecting unit according to the second embodiment in a wearable device according to an embodiment of the present disclosure.
Figure 29:
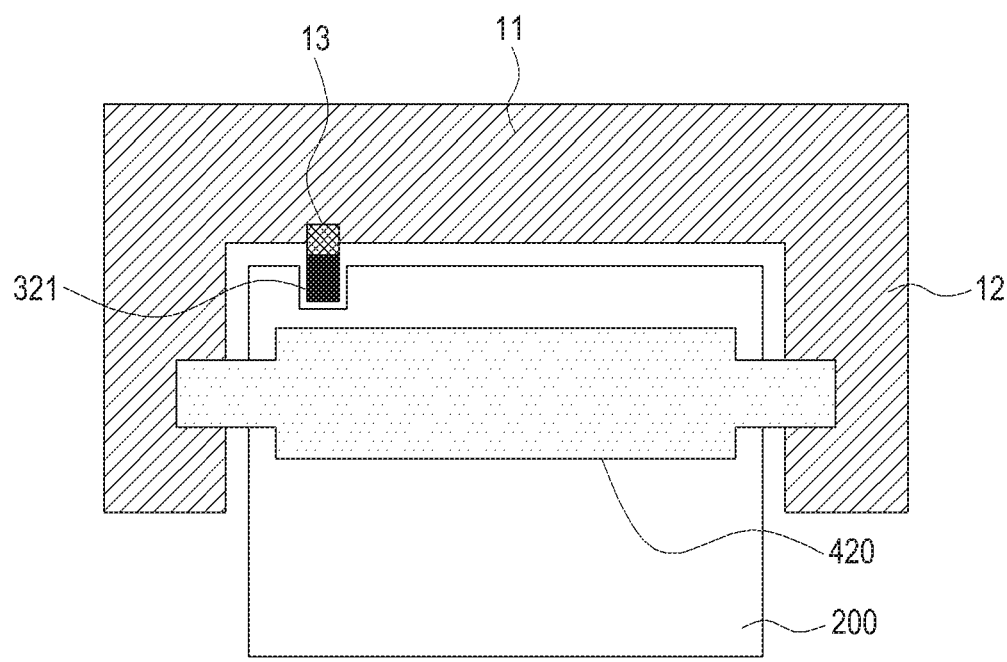
FIG. 29 is a view illustrating a second connecting module being provided in a body portion having a detecting unit according to the second embodiment in a wearable device according to an embodiment of the present disclosure.

FIG. 28 is a view illustrating a first connecting module being provided in a body portion having a detecting unit according to the second embodiment in a wearable device according to an embodiment of the present disclosure FIG. 29 is a view illustrating a second connecting module being provided in a body portion having a detecting unit according to the second embodiment in a wearable device according to an embodiment of the present disclosure.

Referring to FIGS. 28 and 29, the body portion 11 may include a detecting unit 13 that may detect attachment or detachment of the first connecting module 410 or the second connecting module 420. The detecting unit 13 may be provided to detect the attachment or detachment of the second strap portion 200 or to detect the attachment or detachment of at least one of the power supply strap portion 200a or the multi-module strap portion 200b.

The detecting unit 13 may be positioned in the coupled surface between the body portion 11 and the first strap portion 100 or the second strap portion 200. The detecting unit 13 has been described above in connection with FIGS. 18A and 18B, and its function, structure, and operation have been described above, and thus the above description applies here.

Accordingly, when the first strap portion 100 is coupled to the body portion 11 through the first connecting module 410 or the second strap portion 200 is coupled with the body portion 11 through the second connecting module 420, the detecting unit 410 may be operated to determine when the first strap portion 420 or the second strap portion 200 is coupled to the body portion 11, and thus, the detecting unit 13 is pressed or depressed, or whether an electrical signal is applied or when a detecting signal is applied. Thus, whether to apply current to the body terminal portion 11a may be controlled, and malfunctions, including current inflow to the first strap portion 100 due to the coupling of the first strap portion 100 and the second strap portion 200 or a short circuit in the body portion 11 due to application of current to the first strap portion 100, may be prevented.

Figure 30A:
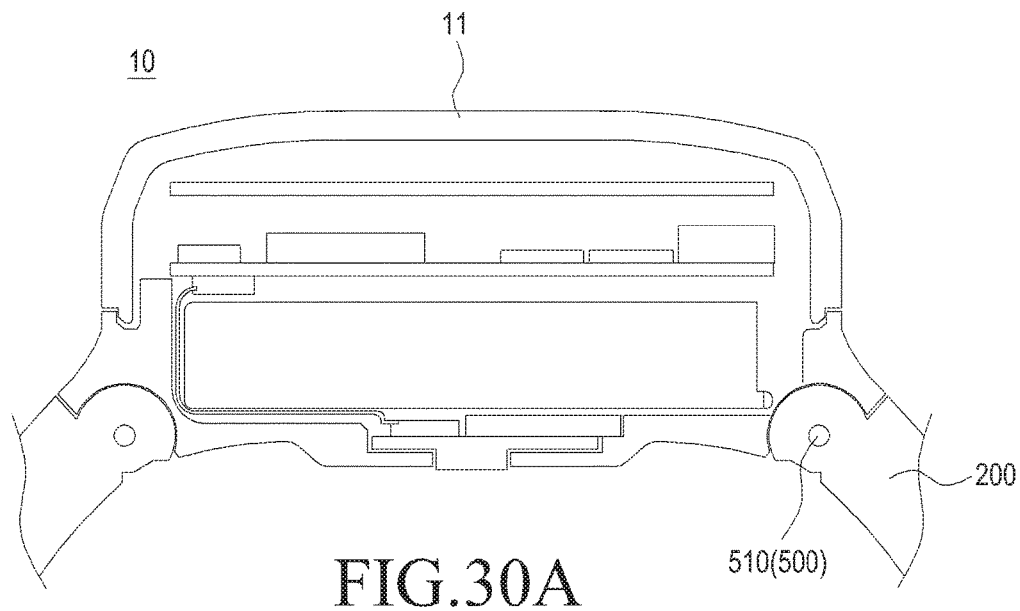
FIGS. 30A and 30B are views illustrating a wearable device having a connecting portion according to a third embodiment of the present disclosure.
Figure 30B:
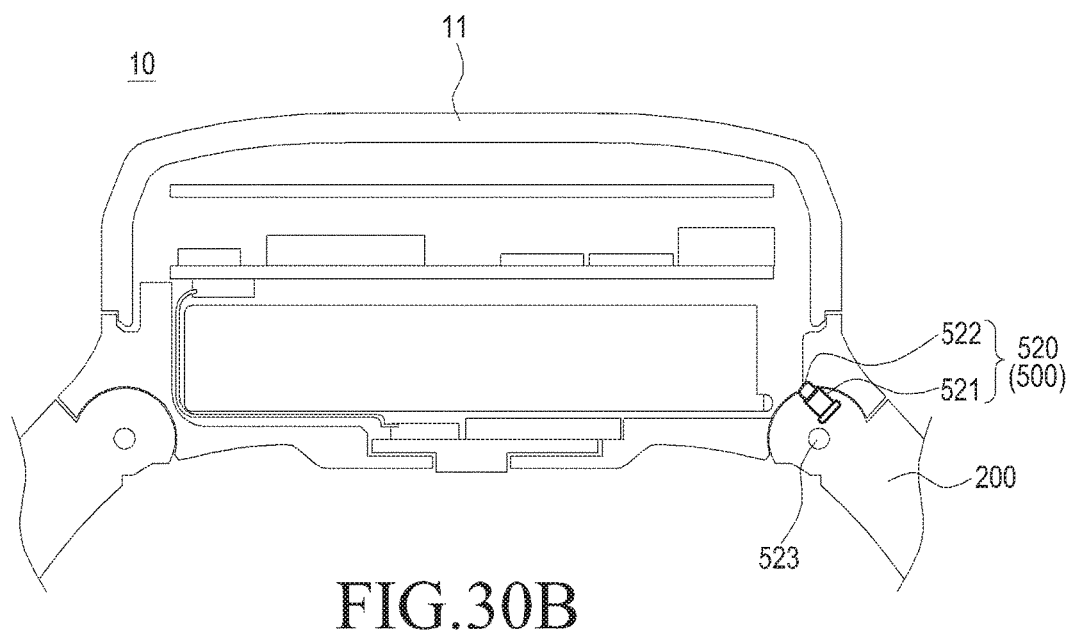
Figure 31:
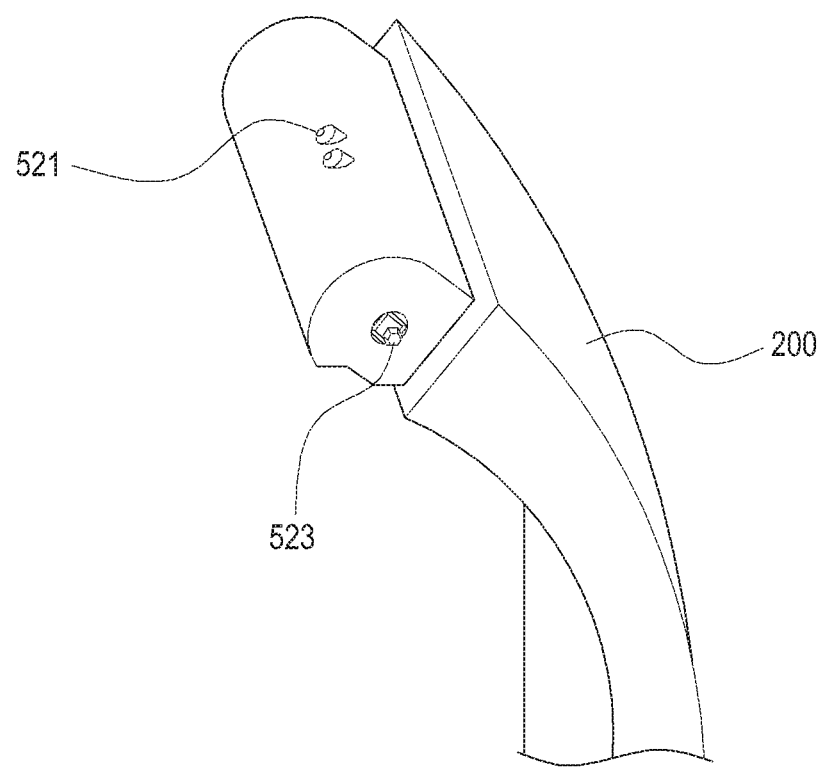
FIG. 31 is a view illustrating a second strap portion according to the third embodiment in a wearable device according to an embodiment of the present disclosure.

FIGS. 30A and 30B are view illustrating a wearable device having a connecting portion according to a third embodiment of the present disclosure. FIG. 31 is a view illustrating a second strap portion according to the third embodiment in a wearable device according to an embodiment of the present disclosure.

Referring to FIGS. 30A and 30B and FIG. 31, the connecting portion 30 (hereinafter, denoted with the reference numeral '500') may include a first coupling portion 510 and a second coupling member 520.

The first coupling portion 510 may be provided to couple the first strap portion 100 to the body portion 11. The first coupling portion 510 may be projectingly provided to be elastically driven toward the coupling portion 12 from both ends of the first strap portion 100. The first coupling portion 510 may be provided to have the same shape as the first connecting module described above in connection with the second embodiment of the present disclosure. However, the shape of the first coupling portion 510 is not limited thereto, and various changes in shape or structure may be made thereto as long as the configuration may connect the body portion 11 with the first strap portion 100.

The second coupling member 520 may include a second coupling portion 523 and pogo pin-type connecting members 521 and 522.

The second coupling portion 523 may be provided to couple the second strap portion 200 to the body portion 11. The second coupling portion 523 may be projectingly provided to be elastically driven toward the coupling portion 12 from both ends of the second strap portion 200. The second coupling portion 523 may be provided to have the same shape or structure as the first connecting module described above in connection with the second embodiment of the present disclosure. However, the shape of the second coupling portion 523 is not limited thereto, and various changes in shape or structure may be made thereto as long as the configuration may connect the body portion 11 with the second strap portion 200.

The pogo pin-type connecting members 521 and 522 may be provided to electrically connect the member 250 with the body portion 11 as the second strap portion 200 is coupled with the body portion 11.

The pogo pin-type connecting members 521 and 522 may include a pogo pin member 521 and a pad portion 522.

The pogo pin member 521 may be provided to be exposed at a surface facing the body portion 11, specifically, the second strap portion 200, and may be provided to be electrically connected to, e.g., a printed circuit board provided in the body portion 11. Further, the pogo pin member 521 may be provided in the body portion 11 by insert bonding or insert molding.

The pad portion 522 may be provided to be exposed at a surface facing the second strap portion 200, specifically, the body portion 11, and may be provided to be electrically connected with the member 250. The pad portion 522 may be provided to contact the pogo pin member 521 to electrically connect the member 250 with the body portion 11.

When the second strap portion 200 is coupled with the body portion 11 through the second coupling portion 523, the pogo pin member 521 and the pad portion 522 are electrically connected with each other, and thus, the function of the member 250 provided in the second strap portion 200 may be implemented through the body portion 11.

Figure 32A:
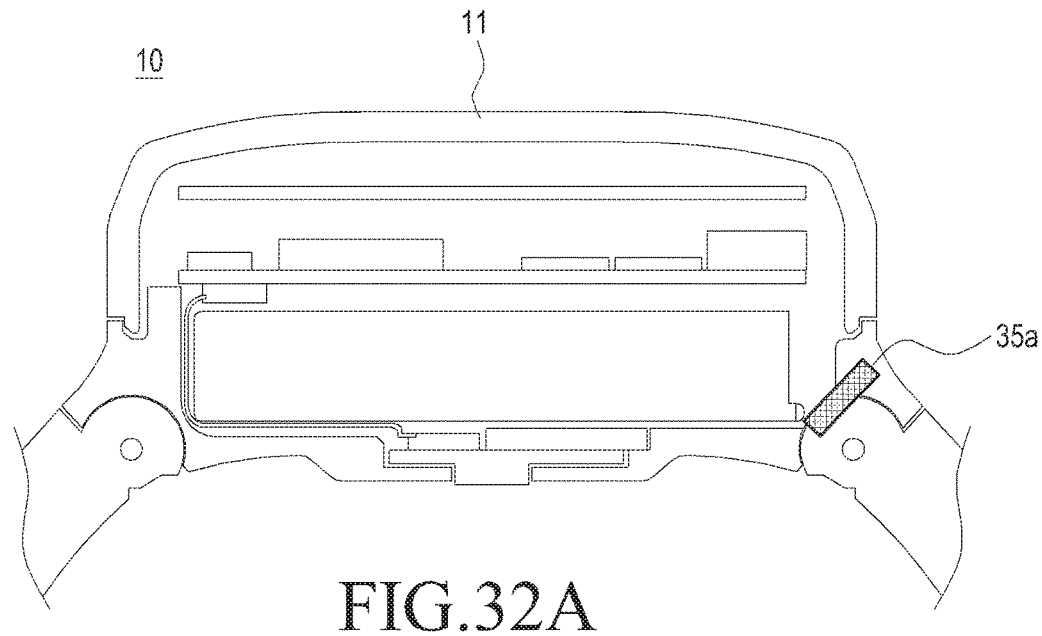
FIGS. 32A and 32B are views illustrating a sealing member provided in a wearable device according to the third embodiment in the wearable device according to an embodiment of the present disclosure.
Figure 32B:
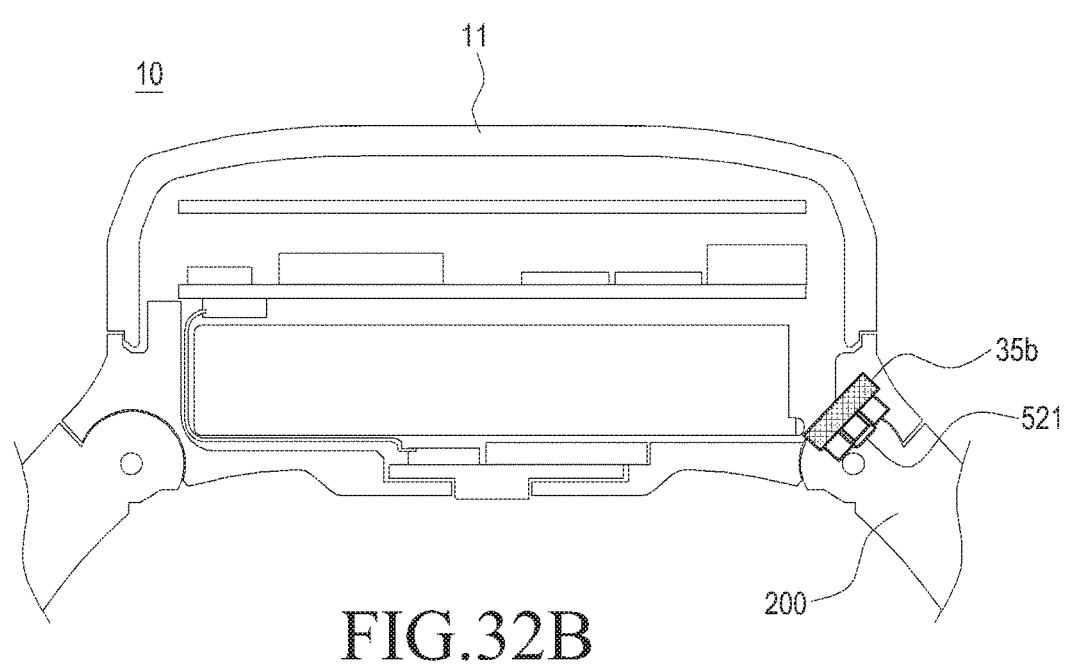

FIGS. 32A and 32B are views illustrating a sealing member provided in a wearable device according to the third embodiment in the wearable device according to an embodiment of the present disclosure.

Referring to FIGS. 32A and 32B, the first sealing member 35a may be provided in the first strap portion 100 and the body portion 11 to seal the coupled surface between the first strap portion 100 and the body portion 11. The first sealing member 35a may be provided to come in tight contact between the first strap portion 100 and the body portion 11 to seal the periphery of the first strap portion 100, specifically the pogo pin member 521.

The second sealing member 35b may be provided to air-tightly seal the periphery of the second coupling member 520, specifically the periphery of the pogo pin member 521 and the pad portion 522. The second sealing member 35b may be projectingly provided at the periphery of the pad portion 522 or the pogo pin member 521 to be tightly contacted as the second strap portion 200 is coupled with the body portion 11.

According to the third embodiment of the present disclosure, the first sealing member 35a and the second sealing member 35b may be provided to include at least one material of rubber, synthetic rubber, silicone, urethane, and the like. The sealing member 35 may be formed of an elastic material as described above, and may thus be brought in tight contact as the body portion 11 is coupled with the first strap portion 100 or second adapter portion 200.

Although not shown, the above-described detecting unit 13 may be provided. The configuration of the detecting unit 13 is the same as the configuration or structure described above, and the above description may apply.

As described above, the body portion 11 according to an embodiment of the present disclosure may have the detecting unit 13 that may detect attachment or detachment of at least one of the first strap portion 100 and the second strap portion 200 or may drive automatic recognition according to the attachment or detachment of the second strap portion 200. For example, according to an embodiment of the present disclosure, the detecting unit 13 may be provided to detect the attachment or detachment of the second strap portion 200 or to detect the attachment or detachment of at least one of the power supply strap portion 200a or the multi-module strap portion 200b. The detecting unit 13 may be implemented in a structure in which automatic recognition is possible by a mechanical configuration or by an electrical configuration.

The structure in which attachment or detachment of the first strap portion 100 or the second strap portion 200 is automatically recognized by a mechanical configuration, specifically, the configuration of the mechanical button switch, has been described above in the embodiments of the present disclosure, and the description may apply here.

The second strap portion 200, particularly, the power supply strap portion 200a or the multi-module strap portion 200b, may be coupled to the body portion 11. First, the power supply strap portion 200a being coupled with the body portion 11 may be described.

Figure 33A:
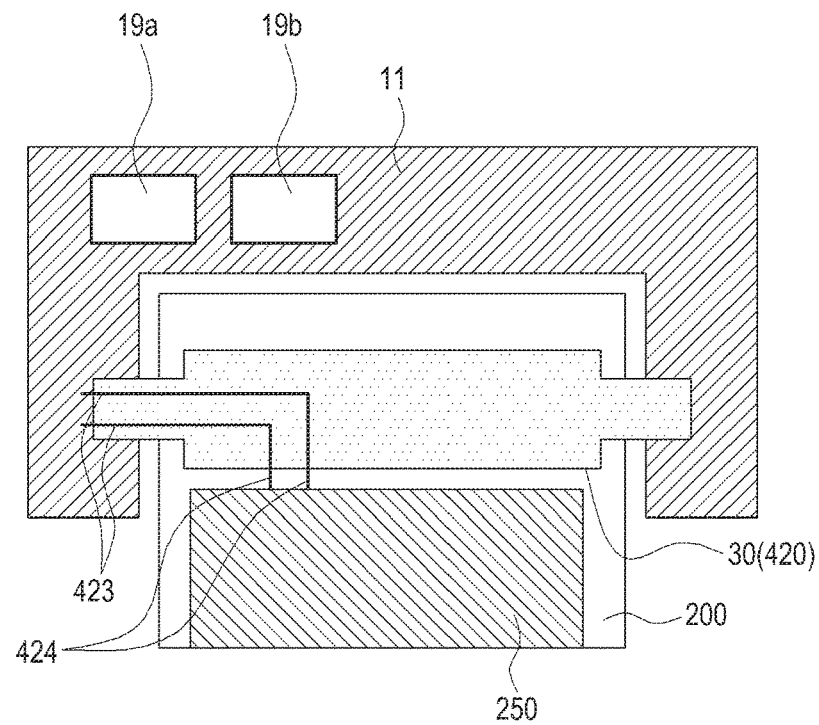
FIGS. 33A and 33B are views illustrating a power supply strap portion being provided in a wearable device according to an embodiment of the present disclosure.
Figure 33B:
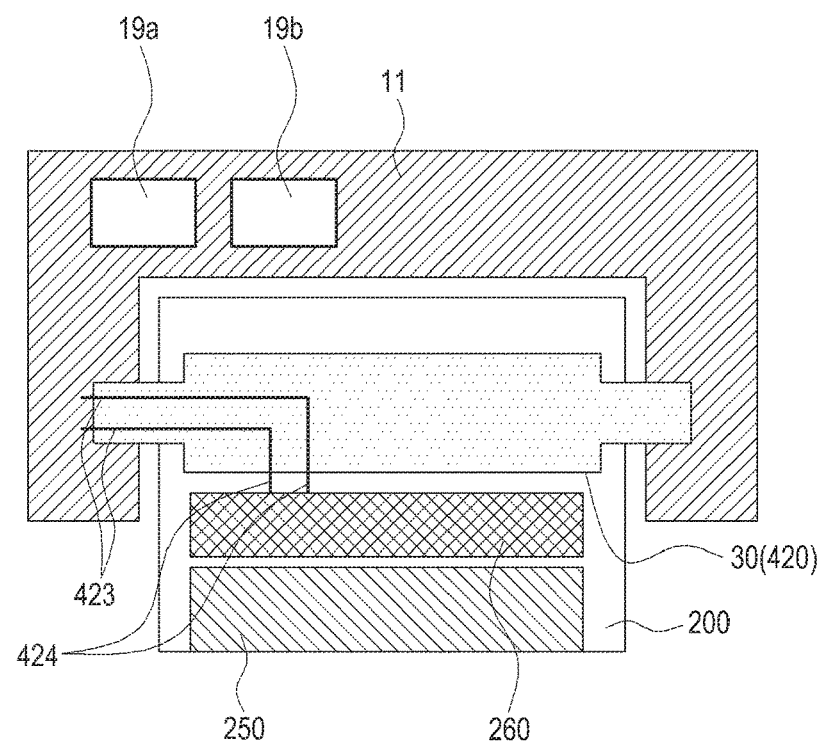
Figure 34:
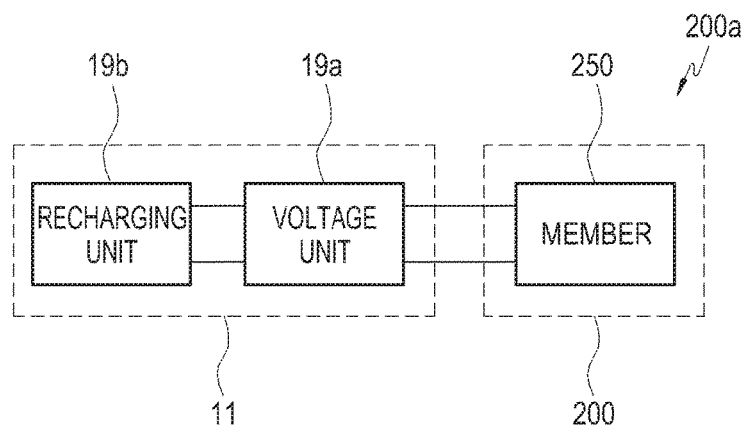
FIG. 34 is a block diagram illustrating a first embodiment of a wearable device having a power supply strap portion according to an embodiment of the present disclosure.
Figure 35:
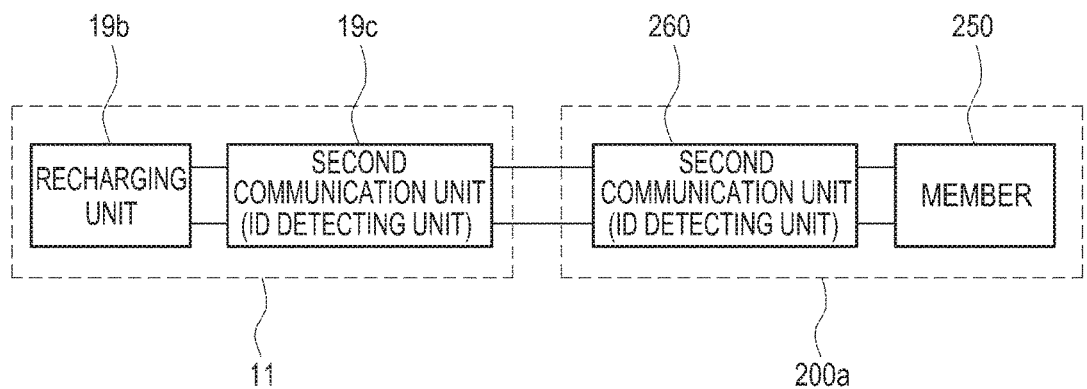
FIG. 35 is a block diagram illustrating a second embodiment of a wearable device having a power supply strap portion according to an embodiment of the present disclosure.

FIGS. 33A and 33B are views illustrating a power supply strap portion being provided in a wearable device according to an embodiment of the present disclosure. FIG. 34 is a block diagram illustrating a first embodiment of a wearable device having a power supply strap portion according to an embodiment of the present disclosure. FIG. 35 is a block diagram illustrating a second embodiment of a wearable device having a power supply strap portion according to an embodiment of the present disclosure.

Referring to FIGS. 33A and 33B to FIG. 35, the body portion 11 may be coupled with the power supply strap portion 200a. When the power supply strap portion 200a is coupled to the body portion 11, the connecting portion 30 may electrically connect the power supply strap portion 200a, specifically, the member 250, with the body portion 11. Hereinafter, the connecting portion 30 is described as provided as the above-described spring pin-type connecting member according to the second embodiment of the present disclosure, for example. However, the connecting portion 30 may have the same shape or structure as described above in connection with the first to third embodiments of the present disclosure, specifically, as the second adapter portion 320, the second connecting module 420, the pogo pin member 521, and the like. Further, the connection terminal portion 30a for connecting the body portion 11 with the member 250 may be provided a two pin-type electrical connection terminal portion. The member 250 may be provided as at least one of a secondary battery, a wireless recharge module, an automatic recharge module, an energy harvesting module, and the like. When the member 250 is provided as one of the secondary battery, a wireless recharge module, an automatic recharge module, an energy harvesting module, and the like, recharging the battery of the body portion 11 by the member 250 may come in two schemes as follows.

First, as shown in FIGS. 33A and 34, the body portion 11 may include a voltage detecting unit 19a for detecting a voltage of the power supply strap portion 200a and a recharging unit 19b for recharging the battery of the body portion 11 depending on a signal detected by the voltage detecting unit 19a. The voltage detecting unit 19a may be provided to detect attachment or detachment of the power supply strap portion 200a when the second strap portion 200 is attached or detached. As the power supply strap portion 200a is coupled to the body portion 11, a voltage is applied to the voltage detecting unit 19a. Further, at least one module of a secondary battery, a wireless recharge module, an automatic recharge module, an energy harvesting module, and the like, mounted in the second strap portion 200, specifically in the power supply strap portion 200a, recharges the battery of the body portion 11 or supplies power to the body portion 11.

Second, as shown in FIGS. 33B and 34, the body portion 11 may include a second communication unit 19c for detecting attachment or detachment of the power supply strap portion 200a and the recharging unit 19b for providing power generated by the member 250 of the power supply strap portion 200a to the body portion 11 or recharging the battery of the body portion 11. The second communication unit 19c may be provided as an identity (ID) detecting unit that may detect a unique identification number generated from a first communication unit 260 that is described below. The ID detecting unit may be provided to detect an individual signal from the member 250 mounted in the power supply strap portion 200a, specifically each module of a secondary battery, a wireless recharge module, an automatic recharge module, an energy harvesting module, and the like. Accordingly, the recharging unit 19b may supply power suitable for each signal to the body portion 11 according to an individual signal from the member 250 mounted in the power supply strap portion 200a.

The power supply strap portion 200a may include the member 250 that supplies power to the body portion 11 or supplies power to recharge the battery in the body portion 11 and a first communication unit 260 that may communicate signals with the second communication unit 19c as it is attached or detached from the body portion 11. The first communication unit 260 may be provided as an ID generating unit having a unique identification number (ID). The member 250 mounted in the power supply strap portion 200a includes the first communication unit 260 having an individual unique identification number. Accordingly, when the power supply strap portion 200a is coupled to the body portion 11, a signal of the unique identification number of the first communication unit 260 is applied to the second communication unit 19c. The second communication unit 19c may detect the signal from the first communication unit 260, and by a signal value according to the same, power from the first communication unit 260 may be provided to the recharging unit 19b.

Figure 36:
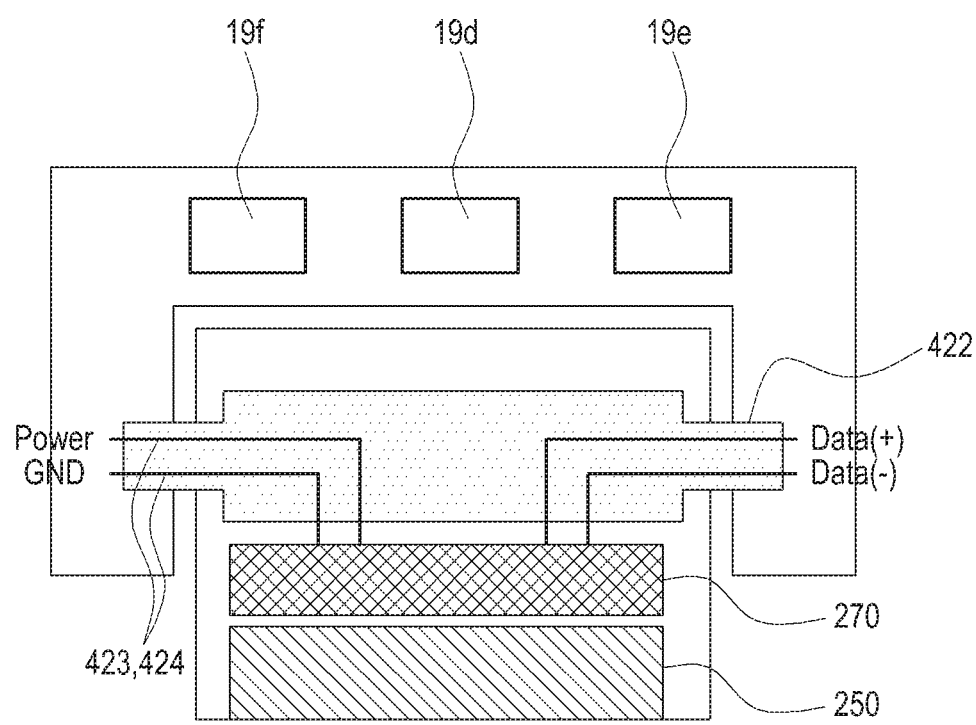
FIG. 36 is a view illustrating a multi-module strap portion being provided in a wearable device according to an embodiment of the present disclosure.
Figure 37:
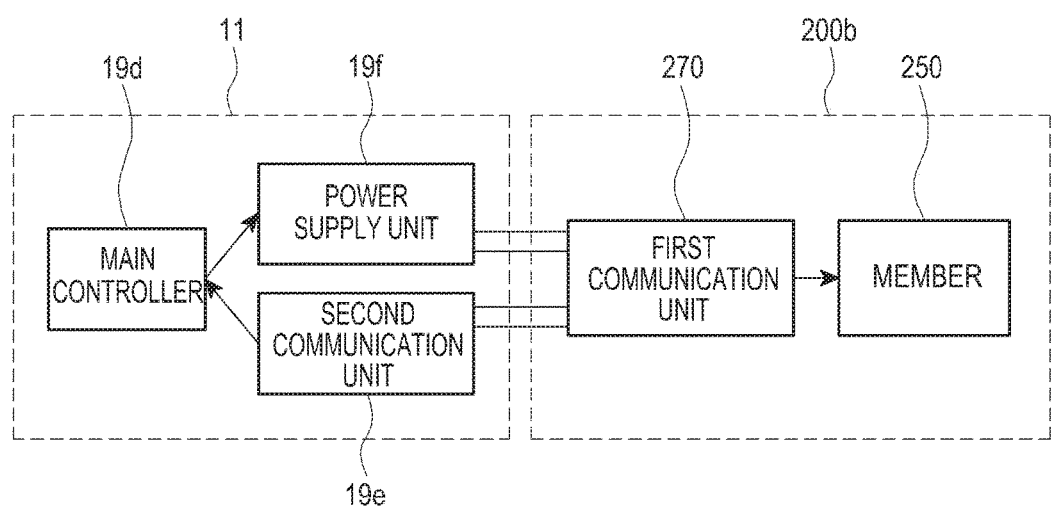
FIG. 37 is a block diagram illustrating a wearable device having a multi-module strap portion according to an embodiment of the present disclosure.

FIG. 36 is a view illustrating a multi-module strap portion being provided in a wearable device according to an embodiment of the present disclosure. FIG. 37 is a block diagram illustrating a wearable device having a multi-module strap portion according to an embodiment of the present disclosure. Hereinafter, the connecting portion 30 is first described as provided as the above-described spring pin-type connecting member according to the second embodiment of the present disclosure, for example. However, the connecting portion 30 may have the same shape or structure as described above in connection with the first to third embodiments of the present disclosure, specifically, as the second adapter portion 320, second connecting module 420, pogo pin member 521, and the like. The connection terminal portion 30a for connecting the body portion 11 with the member 250 may be provided as a four pin-type electrical connection terminal portion that enables data communication while applying power to the member 250.

Referring to FIGS. 36 and 37, the multi-module strap portion 200b may be coupled to the body portion 11. The body portion 11 may include a main controller 19d, a power supply unit 19f, and a second communication unit 19e for performing operations, such as detecting the attachment or detachment of the multi-module strap portion 200b to supply power from the member 250 depending on the detected result or providing a function of the member 250 supplied with power to the body portion 11. The multi-module strap portion 200b does not have its own power source. Accordingly, when the multi-module strap portion 200b is coupled to the body portion 11, the member 250 may receive power from the battery of the body portion 11 to operate. Further, a function of the powered member 250 may be displayed or operated through the connection terminal portion 30a depending on user settings.

Specifically, the multi-module strap portion 200b may include a first communication unit 270 that transfers a signal generated as the body portion 11 is attached or detached to the body portion 11 and the member 250 that provides various multiple functions to the body portion 11. Further, the body portion 11 may include the second communication unit 19e that receives the signal from the first communication unit 270, the power supply unit 19f that supplies power to the member 250 according to the signal value transferred to the second communication unit 19e, and the main controller 19d that receives a signal from the second communication unit 19e to perform control to drive the power supply unit 19f. The second communication unit 19e may be provided as a main communication controller that controls communication with the first communication unit 270, and the first communication unit 270 may be provided as an auxiliary communication controller that may communicate with the main communication controller. When the multi-module strap portion 200b is mounted in the body portion 11, a signal from the first communication unit 270 is applied to the second communication unit 19e. A detected signal value of the first communication unit 270 which is applied to the second communication unit 19e is applied to the main controller 19d. The main controller 19d, after receiving the detected signal value, controls the power supply unit 19f to supply power to the member 250. The power supply unit 19f supplies power to the main controller 19d and the multi-module strap portion 200b, specifically, the member 250, to enable them to turn in an operable state. For example, the member 250 of the multi-module strap portion 200b is activated.

Further, the first communication unit 270 may generate a signal according to each unique identification number by the member 250 mounted in the multi-module strap portion 200b. When the multi-module strap portion 200b is coupled to the body portion 11, the signal of the unique identification number from the first communication unit 270 is applied to the second communication unit 19e. The second communication unit 19e may detect the signal of the first communication unit 270 and may apply the detected signal value to the main controller 19d. The main controller 19d may control the body portion 11 to execute a user function according to the signal of the unique identification number.

Figure 38A:
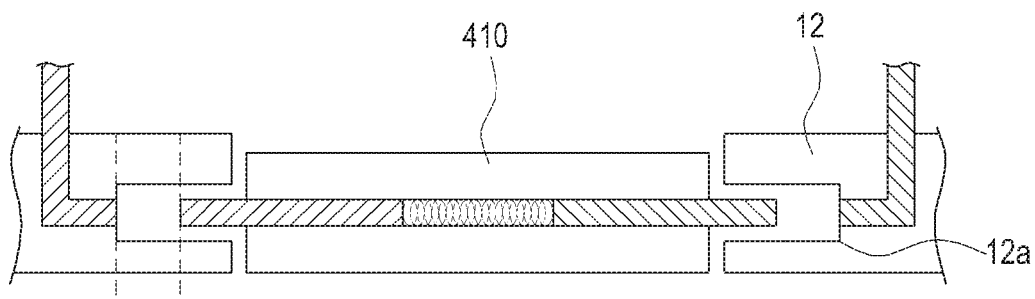
FIGS. 38A and 38B are views schematically illustrating a short circuit preventing unit in a wearable device according to an embodiment of the present disclosure.
Figure 38B:
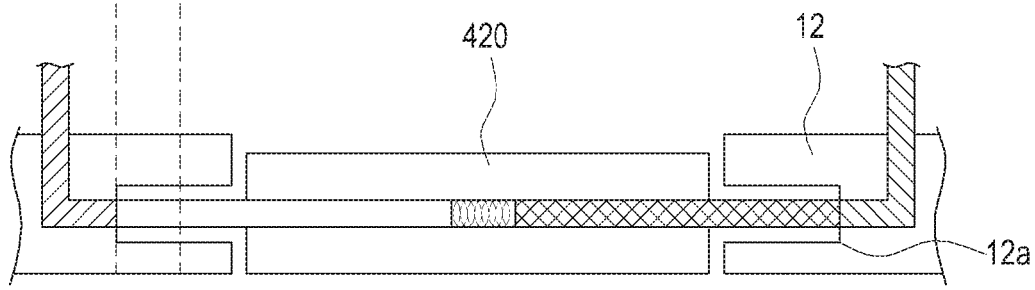

FIGS. 38A and 38B are views schematically illustrating a short circuit preventing unit in a wearable device according to an embodiment of the present disclosure. Hereinafter, the connecting portion 30 is described as provided as the above-described spring pin-type connecting member according to the second embodiment of the present disclosure, for example. However, the connecting portion 30 may have the same shape or structure as described above in connection with the first to third embodiments of the present disclosure, specifically, as the adapter portion 310 and 320, first or second connecting module 410 and 420, or first coupling unit and second coupling member 521, 522, and 523.

Referring to FIGS. 38A and 38B, a short circuit preventing unit 600 may be included between the body portion 11 and the first strap portion 100 to restrict an inflow of electrical signal of the body terminal portion 11a electrically connecting the body portion 11 with the second strap portion 200. According to an embodiment of the present disclosure, the short circuit preventing unit 600 is provided to give a gap in length between the first connecting module 410 and the second connecting module 420. When the second strap portion 200 is connected to the body portion 11, the body terminal portion 11a electrically connected with the second strap portion 200 may be provided in an inside surface of the coupling portion 12a in the body portion 11. Accordingly, a current is being applied to the inside surface of the coupling portion 12a by the body terminal portion 11a. In such state, when the first connecting module 410 is fitted into the coupling portion 12a to contact the inside surface of the coupling portion 12a, a current is applied, and there is no insulation between the end of the first connecting module 410 and the body terminal portion 11a, causing a short circuit. Accordingly, when the first connecting module 410 is provided in the body portion 11, the short circuit preventing unit 600 according to an embodiment of the present disclosure, which may prevent the end of the first connecting module 410 from contacting the body terminal portion 11a, may be implemented by making the length of the first connecting module 410 smaller than the length of the second connecting module 420.

Although not shown, the short circuit preventing unit 600 may be implemented by detecting a coupling of the first strap portion 100 to the body portion 11 through a configuration, such as the above-mentioned detecting unit to short out the current applied to the body terminal portion 11a. Further, when the first strap portion 100 is coupled with the body portion 11, an insulating member (not shown) formed of a rubber material may be provided between the body terminal portion 11a and the first strap portion 100 to insulate the body terminal portion 11a from the first strap portion 100.

As described above, the short circuit preventing unit 600 may be implemented in a mechanical manner or in a circuit-wise manner.

When preventing a short circuit is achieved in a mechanical manner, the first and second connecting modules 410 and 420 may be rendered to have different lengths or a separate insulating member may be provided as described above. Further, although not mentioned, when a connection is made through the above-described adapter portion 300, the short circuit preventing unit 600 may be provided as a space between the first adapter portion 310 and the body terminal portion 11a of the body portion 11 or an insulating member between the body portion 11 and the first adapter portion 310. Accordingly, a contact between the body terminal portion 11a and the first adapter portion 310 may be prevented, and a short circuit may be prevented.

When preventing a short circuit is achieved in a circuit-wise manner, the short circuit preventing unit 600 is provided to apply current to the body terminal portion 11a or restrict application of current to the body terminal portion 11a by the attachment or detachment of the first or second strap portion 100 and 200.

Figure 39:
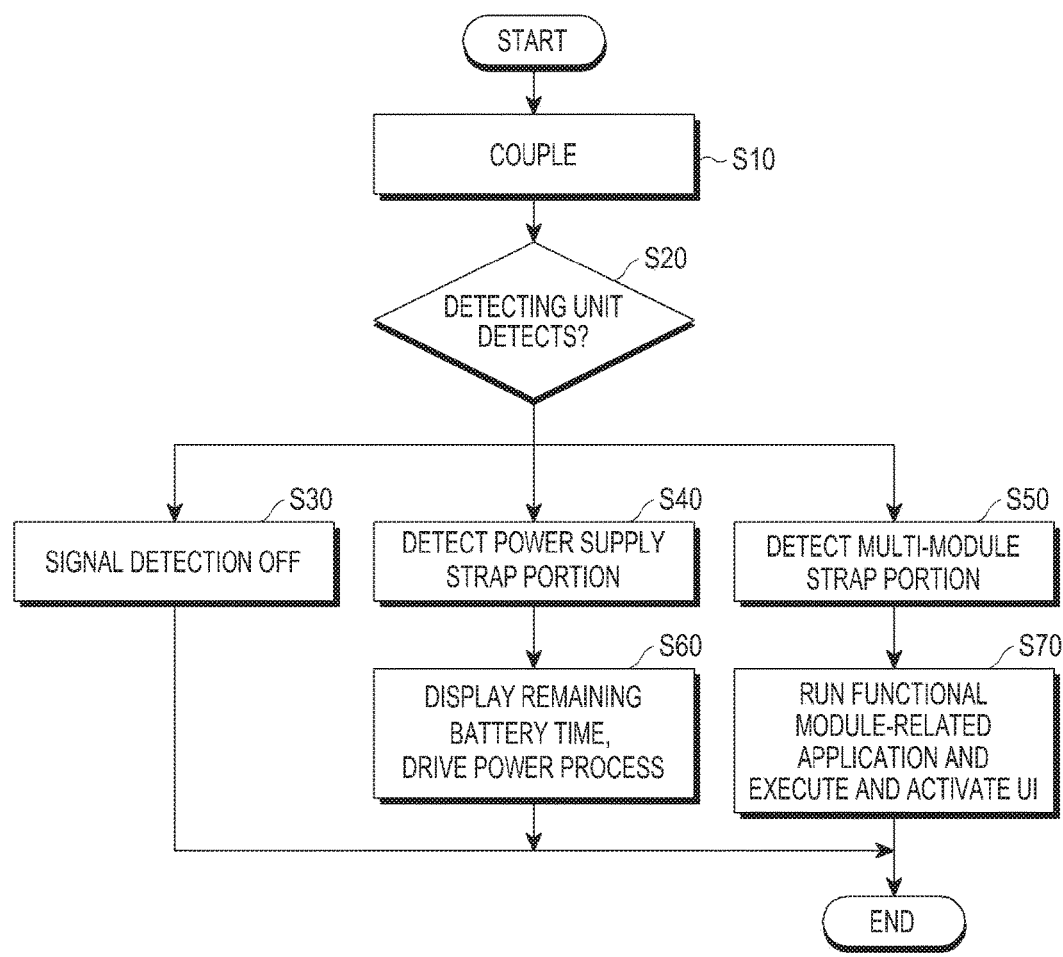
FIG. 39 is a flowchart illustrating a first strap portion or a second strap portion being attached or detached from a body portion in a wearable device according to an embodiment of the present disclosure.

FIG. 39 is a flowchart illustrating a first strap portion or a second strap portion being attached or detached from a body portion in a wearable device according to an embodiment of the present disclosure.

Referring to FIG. 39, at least one of the first strap portion 100 or the second strap portion 200 is coupled to the body portion 11 at operation S10. When the first strap portion 100 or the second strap portion 200 is coupled to the body portion 11, the coupling of the first strap portion 100 or the second strap portion 200 may be detected by a signal value detected by the detecting unit 13 at operation S20. Further, a unique identification number of the second strap portion 200 may be detected through the main controller 19d of the body portion 11, main communication controller or voltage detecting unit or an ID detecting unit. Accordingly, the main controller 19d receives the unique identification number according to the coupling of the first strap portion 100, power supply strap portion 200a or multi-module strap portion 200b to perform control so that a function may be executed according to the received signal value at operations S30, S40, and S50. For example, when the first strap portion 100 is coupled, no signal value is generated, so that no function is executed at operation S30. Further, when the power supply strap portion 200a is coupled to the body portion 11, pairing may occur so that the body portion 11 may be powered at operation S40. Further, when the multi-module strap portion 200b is coupled to the body portion 11, a relevant user setting may be run or activated to be run at operation S50.

Specifically, after recognition the attachment or detachment of the functional strap portion, not a normal strap portion, a relevant application may be automatically executed or may turn in an activated state at operation S70.

For example, when the functional strap portion is connected, the connection of the functional strap portion may be displayed, e.g., in such a manner that a popup window shows up on the body portion 11, and a corresponding application may be activated or a change to a user interface (UI) mode may occur, or a corresponding graphical user interface (GUI) may be displayed with icons on the display portion 11b.

Further, when the functional strap portion is released from the body portion 11, the release of the functional strap portion may be automatically displayed on the display portion 11b of the body portion 11, and the corresponding application may be deactivated or a UI mode change occur or the corresponding GUI may be removed from the display unit 11b.

When the power supply strap portion 200a is attached or detached from the body portion 11, particularly when the power supply strap portion 200a with the battery is attached or detached from the body portion 11, a notification according to the attachment of the power supply strap portion 200a may be displayed on the display portion 11b of the body portion 11. Accordingly, the remaining battery time of the body portion 11 may be displayed on the display portion 11b at operation S60, and a low power mode, such as adjusting the brightness of the display portion 11b, may be released.

Further, when the wireless recharge module of the power supply strap portion 200a is coupled, a window indicating that the wireless recharge module is coupled pops up on the display portion 11b of the body portion 11, wireless recharging may be attempted, and a wireless recharge guide may pop up.

Further, when the multi-module strap portion 200b is connected to the body portion 11, for example, when the multi-module strap portion 200b has a health detection-enabled module, a window indicating that the health detection-enabled multi-module strap portion 200b is connected may be displayed on the display portion 11b through the connecting portion 30. Further, a healthcare-related application may be executed, or an application, such as an application for measuring workout or an application for measuring body fat, may be activated.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:
1. A wearable device, the wearable device comprising:
a body portion of the wearable device;
a connecting portion mechanically securing and electrically connecting the body portion with a first strap portion or mechanically securing and electrically connecting the body portion with a second strap portion;
the first strap portion configured to be attached or detached from the connecting portion and provided to allow the connecting portion to be worn on a human body; and
the second strap portion configured to:
be detachably exchanged with the first strap portion,
be electrically connected to the connecting portion, and
have a battery and at least one member to provide a signal generated from the at least one member to the body portion via the connecting portion, wherein the connecting portion comprises a spring pin-type connecting member, the spring pin-type connecting member including a first connecting module provided between the first strap portion and the body portion and detachably coupling the first strap portion to the body portion via the connecting portion, and wherein the first connecting module comprises:
a first pin body pulled in between the first strap portion and the body portion, and
first protrusion portions provided to project from both ends of the first pin body, at least one of the first protrusion portions elastically driven from the first pin body.

2. The wearable device of claim 1, wherein the members comprise at least one of a module providing body information to the body portion via the connecting portion, or a module providing multiple functions to the body portion via the connecting portion.

3. The wearable device of claim 2,
wherein the members comprise, at least one of a body information detecting module, an energy harvesting module, an automatic contacting module, a wireless recharge module, an automatic recharge module, a light emission module, a global positioning system (GPS) module, a camera module, a speaker module, a haptic module, or a put-on-body detecting module, and
wherein the second strap portion comprises at least one member having the function.

4. The wearable device of claim 2, wherein the second strap portion comprises:
a power supply strap portion allowing the members to supply power to the main body or having an own power source; and
a multi-module strap portion receiving power from the main body and providing multiple functions to the main body.

5. The wearable device of claim 4, wherein the main body further comprises a detecting device configured to detect attachment or detachment of the second strap portion or attachment or detachment of at least one of the power supply strap portion or the multi-module strap portion.

6. The wearable device of claim 5, wherein the detecting device comprises at least one of a mechanical button switch, a pogo terminal portion, a pressure sensor, or a hall sensor.

7. The wearable device of claim 6,
wherein, when the first strap portion is coupled to the body portion via the connecting portion, the detecting device is further configured to detect a signal indicating the coupling of the first strap portion according to at least any one of whether to be pressed, whether an electrical signal is applied, and whether a detecting signal is applied, and
wherein, when the second strap portion is coupled to the body portion via the connecting portion, the detecting device is further configured to detect a signal indicating the coupling of the second strap portion through an opposite operation of an operation performed when the first strap portion is coupled, and the body portion controls an operation of the member by recognizing the second strap portion.

8. The wearable device of claim 7,
wherein at least one of the first strap portion or the second strap portion is coupled to the body portion via the connecting portion, and
wherein according to a signal value detected by the detecting device, the body portion controls a user setting as the first strap portion is coupled to the body portion via the connecting portion, controls the user setting as the power supply strap portion is coupled, or controls the user setting as the multi-module strap portion is coupled.

9. The wearable device of claim 4,
wherein the power supply strap portion is coupled to the body portion via the connecting portion, and
wherein the detecting device comprises a voltage detecting device configured to detect a voltage of the power supply strap portion and a recharging circuit configured to recharge the battery of the body portion according to a signal detected by the voltage detecting device.

10. The wearable device of claim 4,
wherein the power supply strap portion is coupled to the body portion via the connecting portion,
wherein the power supply strap portion comprises a first communication circuit configured to transfer a signal generated according to attachment or detachment from the body portion to the body portion via the connecting portion, and
wherein the detecting device comprises a second communication circuit configured to receive a signal from the first communication circuit and a recharging circuit configured to recharge the battery of the body portion according to a signal value transferred to the second communication circuit.

11. The wearable device of claim 10, wherein the connecting portion comprises a two pin-type electrical connection terminal.

12. The wearable device of claim 4,
wherein the multi-module strap portion is coupled to the body portion via the connecting portion,
wherein the multi-module strap portion comprises a first communication circuit configured to transfer a signal generated by attachment or detachment of the multi-module strap portion to the body portion via the connecting portion, and
wherein the body portion comprises a second communication circuit configured to receive a signal from the first communication circuit and at least one processor configured to supply power to the member and recharge the battery of the body portion receiving a signal from the member according to a signal value transferred to the second communication circuit.

13. The wearable device of claim 12, wherein the connecting portion comprises a four pin-type electrical connection terminal that communicates the signal from the member with the body portion provides power to the member.

14. The wearable device of claim 1, wherein the first strap portion and the second strap portion are formed of at least one material of a metal, leather, silicone, urethane, ceramic, or fabric or of at least one material of a metal mixed with a mineral powder comprising at least one of tourmaline, ceramic, jade, germanium, leather, silicone, urethane, ceramic, or fabric.

15. The wearable device of claim 1, wherein the second strap portion comprises at least one of a one-body strap including one piece in which a band for fixing and a band for adjustment are connected with each other or a separable strap including a separable body in which an end and another end are separated or coupled with each other.

16. The wearable device of claim 15,
wherein the body portion comprises the first strap portion, and
wherein the connecting portion comprises a first adapter portion detachably connecting the first strap portion to the body portion via the connecting portion.

17. The wearable device of claim 16, wherein the first adapter portion is provided to surround a surface of the body portion or between an end of the band for fixing and the body portion and between an end of the band for adjustment and the body portion.

18. The wearable device of claim 16, wherein a sealing member is further provided in the first adapter portion to prevent a foreign material from entering a body terminal portion provided in the body portion.

19. The wearable device of claim 15,
wherein the connecting portion is seated surrounding a rear surface of the body portion and comprises a connection terminal portion connected with a body terminal portion provided at a surface of the body portion, and
wherein a second adapter portion is provided to be connected with the band for fixing and the band for adjustment between the band for fixing and the band for adjustment as a single body or to be separated.

20. The wearable device of claim 15,
wherein the connecting portion is provided at an end of the band for fixing and an end of the band for adjustment and comprises a pair of connection terminal portions electrically connected with the body terminal portion provided at both ends of the body portion, and
wherein the second adapter portion is provided at the end of the band for fixing and at the end of the band for adjustment as a single body or to be separated.

21. The wearable device of claim 19, wherein a sealing member is further included between the body terminal portion and the connection terminal portion.

22. The wearable device of claim 21, wherein the sealing member comprises at least one of a rubber material, a silicone material, a urethane material, or a synthetic resin material.

23. The wearable device of claim 15,
wherein the second strap portion further comprises a bezel portion surrounding the body portion, and
wherein the band for fixing and the band for adjustment are detachably coupled to the bezel portion.

24. The wearable device of claim 1, wherein the spring pin-type connecting member further comprises:
a second connecting module compatibly provided with the first connecting module, provided between the second strap portion and the body portion, and electrically coupling the body portion with the second strap portion so that a signal from the member is transferred to the body portion via the connecting portion.

25. The wearable device of claim 24, wherein the first connecting module further comprises:
a first lever portion provided in the first pin body and projected from an inside of the first pin body to an outside of the body portion to drive the first protrusion portions.

26. The wearable device of claim 25, wherein the second connecting module comprises:
a second pin body pulled in between the first strap portion and the body portion;
second protrusion portions provided to project from both ends of the second pin body, at least one of the second protrusion portions elastically driven from the second pin body;
a connecting pin portion provided in the second protrusion portions and electrically connecting the body portion with the second strap portion; and
a connector pin portion provided in the second pin body, provided to project to an inside of the second strap portion, and electrically connecting the connecting pin portion with the member.

27. The wearable device of claim 26, wherein the connecting pin portion and the connector pin portion comprise at least any one of a two pin-type or a four pin-type.

28. The wearable device of claim 26, wherein the second pin body and the second protrusion portions further comprise an insulation coating layer.

29. The wearable device of claim 26,
wherein a first sealing member is provided in the first strap portion and the body portion to seal a coupled surface between the first strap portion and the body portion, and
wherein a second sealing member is provided in the second strap portion and the body portion to seal a coupled surface between the second strap portion and the body portion.

30. The wearable device of claim 1, wherein a short circuit preventing circuit is further included between the body portion and the first strap portion to restrict an inflow of an electrical signal of a body terminal portion electrically connecting the body portion with the second strap portion.

31. The wearable device of claim 30,
wherein the short circuit preventing circuit is provided in a coupling portion where the connecting portion is mounted, and
wherein the connecting portion is provided to restrict a contact short circuit depending on whether the coupling portion has a contact.

32. The wearable device of claim 30, wherein the short circuit preventing circuit is provided to restrict a short circuit by deactivating power supply depending on whether there is power supply pairing between the body portion and the first and second strap portions according to attachment or detachment of the first and second strap portions.

33. A wearable device, the wearable device comprising:
a body portion of the wearable device;
a connecting portion mechanically securing and electrically connecting the body portion with a first strap portion or mechanically securing and electrically connecting the body portion with a second strap portion;
the first strap portion configured to be attached or detached from the connecting portion and provided to allow the connecting portion to be worn on a human body; and
the second strap portion configured to:
be detachably exchanged with the first strap portion,
be electrically connected to the connecting portion, and
have a battery and at least one member to provide a signal generated from the at least one member to the body portion via the connecting portion,
wherein the connecting portion comprises:
a first coupling portion coupling the first strap portion with the body portion; and
a second coupling portion coupling the second strap portion with the body portion, and a pogo pin-type connecting member electrically connecting the member with the body portion according to coupling of the body portion.

34. The wearable device of claim 33, wherein the pogo pin-type connecting member comprises:
a pogo pin member provided in the body portion by insert bonding or insert molding; and a pad portion provided in the second strap portion and contacting the pogo pin member to be electrically connected with the pogo pin member.

35. The wearable device of claim 34,
wherein the first strap portion further comprises a first sealing member tightly contacting a periphery of the pogo pin member, and
wherein a second sealing member is projectingly provided at a periphery of the pad portion to tightly contact the periphery of the pogo pin member.

36. The wearable device of claim 35, wherein the first sealing member and the second sealing member comprise at least one of a rubber material, a silicone material, a urethane material, or a synthetic resin material.

\* \* \* \* \*